United States Patent
Witte et al.

(10) Patent No.: US 11,589,913 B2
(45) Date of Patent: Feb. 28, 2023

(54) VESSEL SEALER WITH HEATING AND COOLING CAPABILITIES

(71) Applicant: Auris Health, Inc., Redwood City, CA (US)

(72) Inventors: Spencer James Witte, Los Altos, CA (US); Luis Andrade Baez, Jr., Mountain View, CA (US); Christopher Allen Julian, Los Gatos, CA (US); Thomas R. Jenkins, Alameda, CA (US); Gregory Tse, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 352 days.

(21) Appl. No.: 16/737,192

(22) Filed: Jan. 8, 2020

(65) Prior Publication Data
US 2020/0237423 A1   Jul. 30, 2020

Related U.S. Application Data

(60) Provisional application No. 62/797,128, filed on Jan. 25, 2019.

(51) Int. Cl.
*A61B 18/08*       (2006.01)
*A61B 34/30*       (2016.01)
(Continued)

(52) U.S. Cl.
CPC ........ *A61B 18/085* (2013.01); *A61B 18/1445* (2013.01); *A61B 18/22* (2013.01);
(Continued)

(58) Field of Classification Search
CPC .............. A61B 18/085; A61B 18/1445; A61B 2017/320095; A61B 2018/044; H05B 1/025
See application file for complete search history.

(56) References Cited

U.S. PATENT DOCUMENTS 3,763,860 A   10/1973   Clarke
4,040,413 A    8/1977   Ohshiro
(Continued)

FOREIGN PATENT DOCUMENTS

CN     101443069    5/2009
EP       1 321 106  6/2003
(Continued)

OTHER PUBLICATIONS

International search report and written opinion dated Mar. 31, 2020 in application No. PCT/US20/12691.

*Primary Examiner* — Gary Jackson
*Assistant Examiner* — Zahed Kabir
(74) *Attorney, Agent, or Firm* — Morgan, Lewis & Bockius LLP

(57) ABSTRACT

Certain aspects relate to systems, devices and techniques for vessel sealing and cutting. In particular, an instrument is provided that is capable of performing multiple functions, including sealing and cutting. The instrument can be robotically controlled, and can include a shaft, a multi-DOF wrist, and an end effector. The end effector is capable of generating and delivering heat via different energy modalities to perform the various functions at different temperatures.

14 Claims, 40 Drawing Sheets

(51) Int. Cl.
  *A61B 18/22* (2006.01)
  *A61B 18/14* (2006.01)
  *A61B 18/00* (2006.01)
  *A61B 17/00* (2006.01)
  *A61B 34/00* (2016.01)
  *A61B 18/04* (2006.01)

(52) U.S. Cl.
  CPC .............. *A61B 34/30* (2016.02); *A61B 34/71* (2016.02); *A61B 2017/00199* (2013.01); *A61B 2018/00023* (2013.01); *A61B 2018/0063* (2013.01); *A61B 2018/00101* (2013.01); *A61B 2018/00345* (2013.01); *A61B 2018/00482* (2013.01); *A61B 2018/00517* (2013.01); *A61B 2018/00541* (2013.01); *A61B 2018/00595* (2013.01); *A61B 2018/00601* (2013.01); *A61B 2018/044* (2013.01); *A61B 2034/256* (2016.02); *A61B 2034/305* (2016.02); *A61B 2218/002* (2013.01); *A61B 2218/007* (2013.01)

(56) References Cited

U.S. PATENT DOCUMENTS

| | | | |
|---|---|---|---|
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |
| 4,747,405 A | 5/1988 | Leckrone |
| 4,854,301 A | 8/1989 | Nakajima |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,788,667 A | 8/1998 | Stoller |
| 5,792,165 A | 8/1998 | Klieman |
| 5,797,900 A | 8/1998 | Madhani |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,183,435 B1 | 6/2001 | Bumbalough et al. |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 7,282,055 B2 | 10/2007 | Tsuruta |
| 7,559,934 B2 | 7/2009 | Teague et al. |
| 7,736,356 B2 | 6/2010 | Cooper et al. |
| 7,963,911 B2 | 6/2011 | Turliuc |
| 7,987,046 B1 | 7/2011 | Peterman |
| 8,002,713 B2 | 8/2011 | Heske |
| 8,038,598 B2 | 10/2011 | Khachi |
| 8,092,397 B2 | 1/2012 | Wallace et al. |
| 8,187,173 B2 | 5/2012 | Miyoshi |
| 8,257,303 B2 | 9/2012 | Moll et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,820,603 B2 | 9/2014 | Shelton et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 9,345,456 B2 | 5/2016 | Tsonton et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,350,390 B2 | 7/2019 | Moll et al. |
| 10,383,765 B2 | 8/2019 | Alvarez et al. |

(56) References Cited

U.S. PATENT DOCUMENTS

| | | |
|---|---|---|
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,639,114 B2 | 5/2020 | Schuh |
| 2002/0019644 A1 | 2/2002 | Hastings |
| 2002/0062123 A1* | 5/2002 | McClurken ........ A61B 18/1442 606/34 |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0125734 A1* | 7/2003 | Mollenauer .......... A61B 18/085 606/51 |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2010/0004642 A1 | 1/2010 | Lumpkin |
| 2010/0010504 A1 | 1/2010 | Simaan et al. |
| 2010/0011900 A1* | 1/2010 | Burbank ................ A61B 34/71 74/490.06 |
| 2010/0011901 A1 | 1/2010 | Burbank |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0282339 A1* | 11/2011 | Weizman ............. A61B 18/148 606/41 |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1 | 12/2013 | Brown |
| 2014/0005681 A1* | 1/2014 | Gee ................ A61B 17/320092 606/130 |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |

(56) References Cited

U.S. PATENT DOCUMENTS

| | | |
|---|---|---|
| 2014/0194905 A1 | 7/2014 | Kappel |
| 2014/0243849 A1 | 8/2014 | Saglam |
| 2014/0275956 A1 | 9/2014 | Fan |
| 2014/0276723 A1 | 9/2014 | Parihar |
| 2014/0276956 A1 | 9/2014 | Crainich |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2015/0080879 A1 | 3/2015 | Trees |
| 2015/0127045 A1 | 5/2015 | Prestel |
| 2015/0133960 A1 | 5/2015 | Lohmeier |
| 2015/0164522 A1 | 6/2015 | Budiman |
| 2015/0201917 A1 | 7/2015 | Snow |
| 2015/0202085 A1 | 7/2015 | Lemonis |
| 2015/0265347 A1* | 9/2015 | Yates ................ A61B 18/18 606/50 |
| 2015/0314110 A1 | 11/2015 | Park |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0095234 A1 | 4/2017 | Prisco et al. |
| 2017/0095295 A1 | 4/2017 | Overmyer |
| 2017/0119481 A1 | 5/2017 | Romo et al. |
| 2017/0135706 A1 | 5/2017 | Frey |
| 2017/0151416 A1 | 6/2017 | Kutikov |
| 2017/0165011 A1 | 6/2017 | Bovay et al. |
| 2017/0172553 A1 | 6/2017 | Chaplin |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258513 A1* | 9/2017 | Lau ................ A61B 18/085 |
| 2017/0265923 A1 | 9/2017 | Privitera |
| 2017/0290631 A1 | 10/2017 | Lee et al. |
| 2017/0319289 A1 | 11/2017 | Neff et al. |
| 2017/0340396 A1 | 11/2017 | Romo et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0177556 A1 | 6/2018 | Noonan et al. |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129222 A1* | 4/2020 | Stringham ............ H05B 1/025 |
| 2020/0146769 A1 | 5/2020 | Eyre |
| 2020/0163726 A1 | 5/2020 | Tanner |

FOREIGN PATENT DOCUMENTS

| | | |
|---|---|---|
| EP | 1 849 423 | 10/2007 |
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |

* cited by examiner

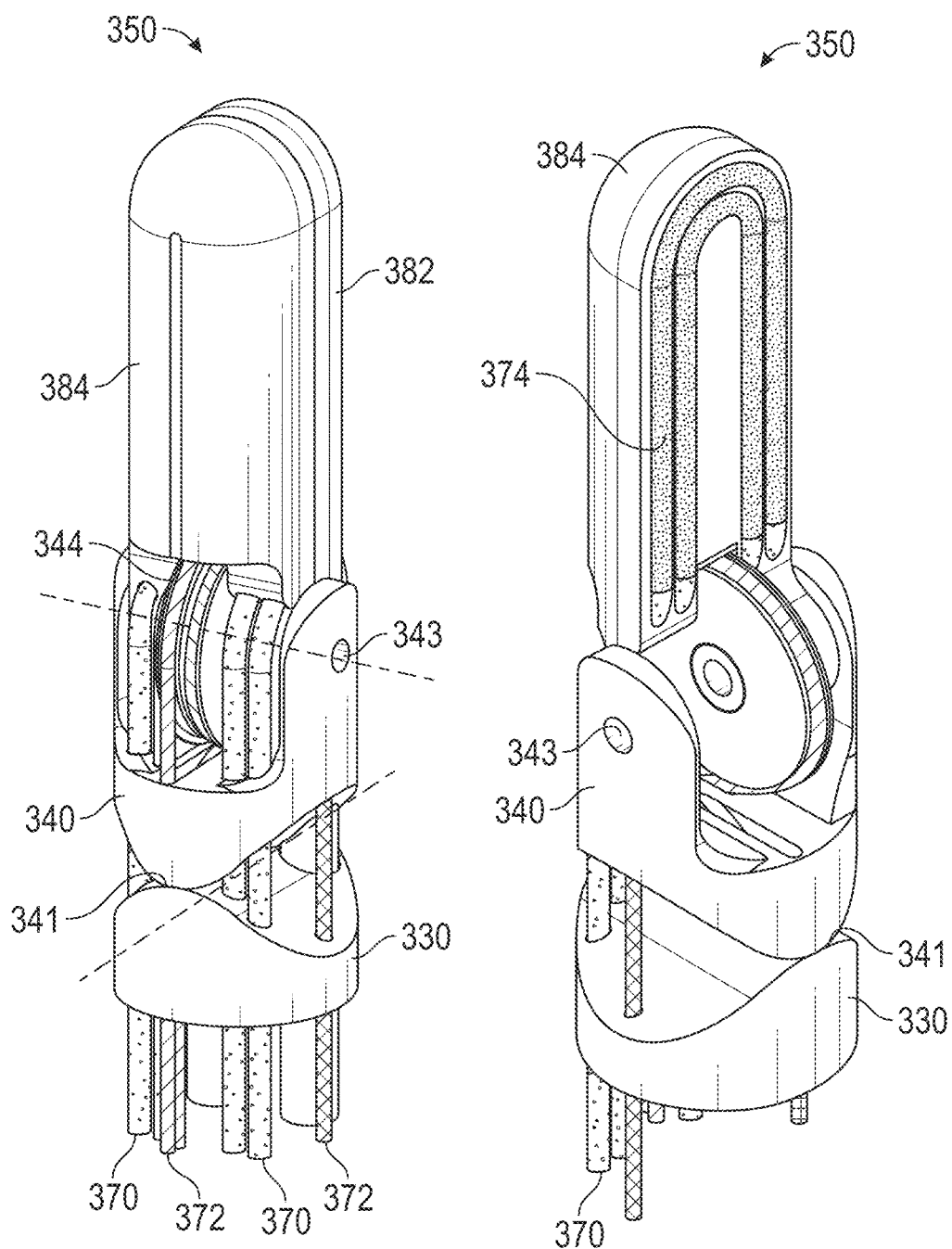

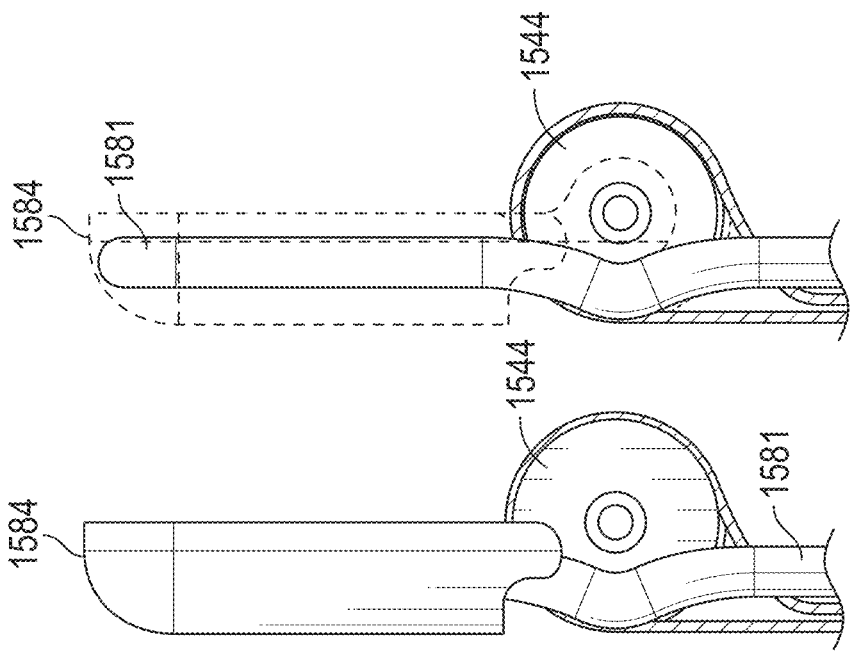
FIG. 55
FIG. 56
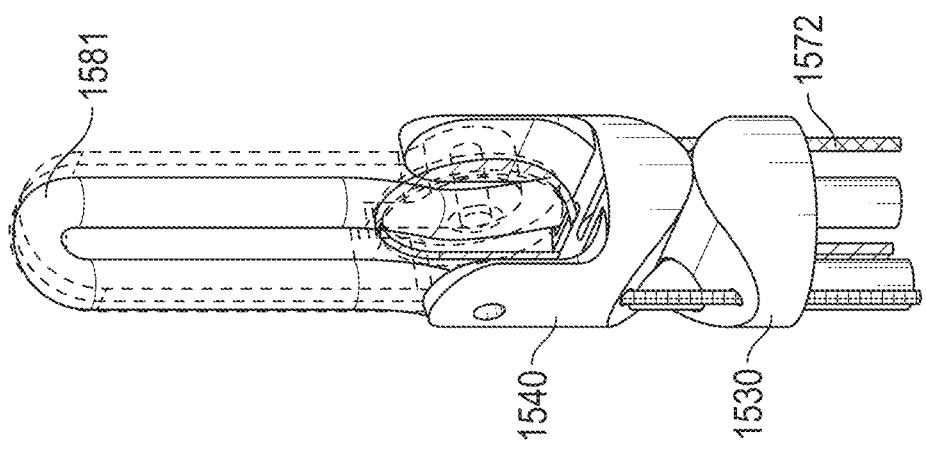
FIG. 54
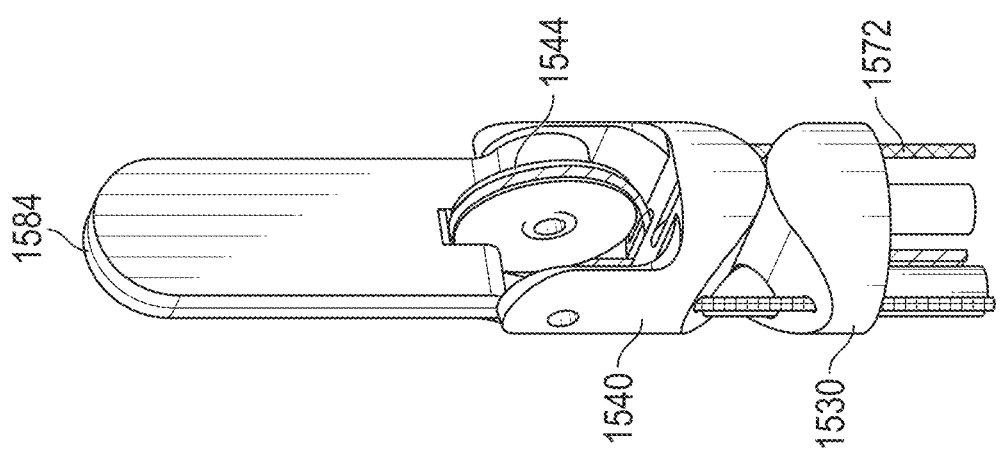
FIG. 53

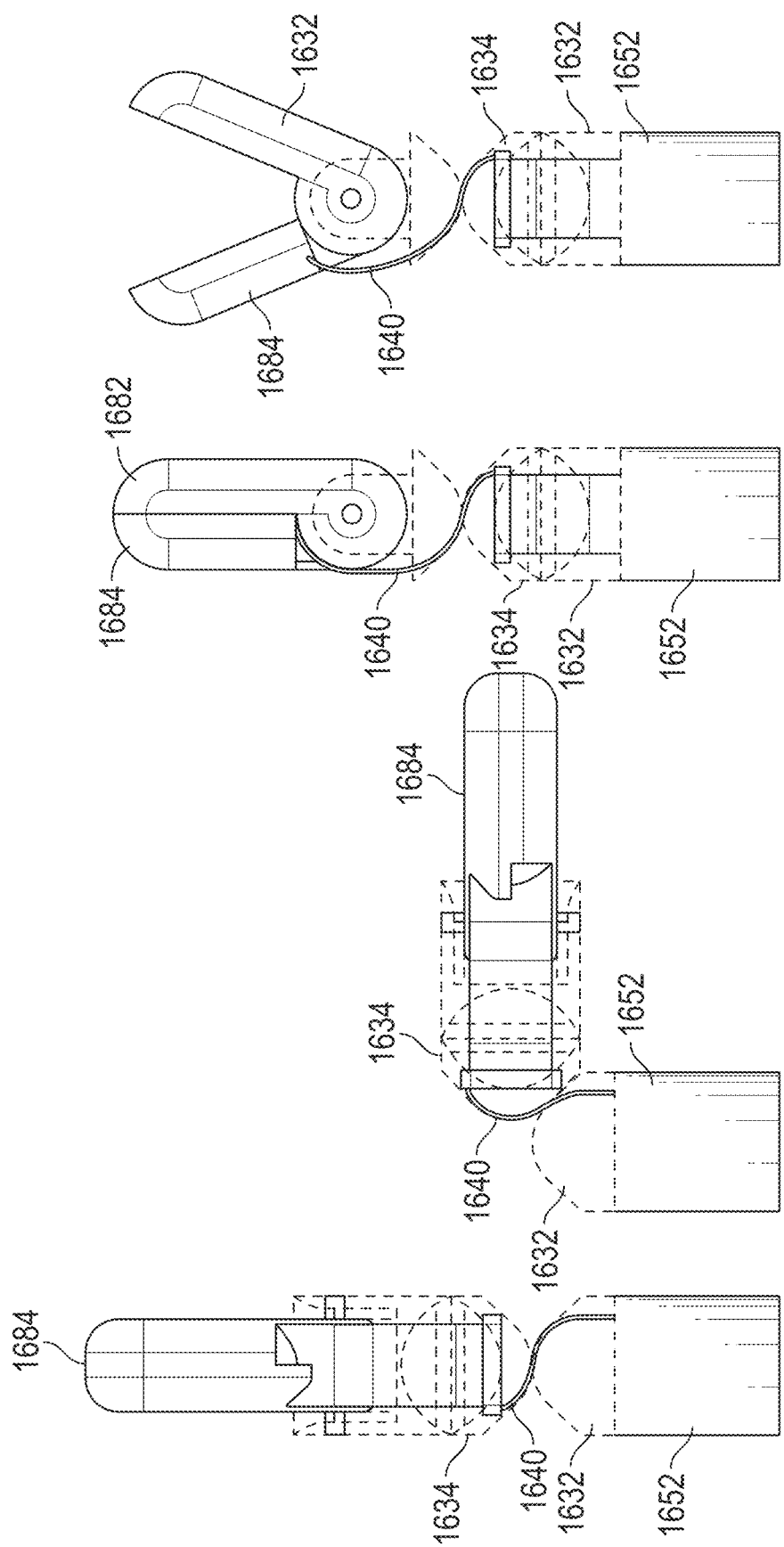

VESSEL SEALER WITH HEATING AND COOLING CAPABILITIES

CROSS-REFERENCE TO RELATED APPLICATION(S)

This application claims the benefit of U.S. Provisional Application No. 62/797,128 filed Jan. 25, 2019, which is hereby incorporated by reference in its entirety.

TECHNICAL FIELD

The systems and methods disclosed herein are directed to medical instruments, and more particularly to robotically controlled medical instruments.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically-enabled medical system may be used to control the insertion and/or manipulation of the medical instrument and end effector. The robotically-enabled medical system may include a robotic arm or any other instrument positioning device. The robotically-enabled medical system may also include a controller used to control the positioning of the instrument during the procedure.

SUMMARY

This disclosure relates to multi-functional medical instruments, as well as to related systems and methods. The multi-functional instruments can be configured to perform several functions during laparoscopic procedures, including cutting and sealing tissue by generating heat for cutting and sealing.

In a first aspect, a multi-functional medical instrument includes a shaft, a wrist coupled to the shaft, the wrist movable in at least two degrees of freedom, and an end effector configured to generate heat to perform at least two different functions.

In one aspect, the end effector may be capable of generating heat to perform sealing and cutting. The end effector may not include a blade. The end effector may include a first jaw and a second jaw, wherein at least one of the first jaw and second jaw includes a conductive member coated with a ferromagnetic coating. The conductive member may include a pad. The conductive member may include a conductive line or coil. The instrument may include an insulative coating positioned between the conductive line and ferromagnetic coating. The ferromagnetic coating may be distributed intermittently along a length of the conductive member. The thickness of the ferromagnetic coating may vary along the length of the conductive member.

In another aspect, the end effector may generate heat via fluidics. The end effector may include a fluid conduit for circulating heated fluid for sealing and a cutting nozzle for delivering heated fluid for cutting. The end effector may include a first jaw and a second jaw, wherein the first jaw may be coupled to fixed electrodes and the second jaw may be coupled to rotating electrodes. The end effector may include a first jaw and a second jaw, and a laser fiber, wherein the first jaw and the second jaw are configured for sealing and the laser fiber is configured for cutting. The first jaw and the second jaw may each be in the shape of a fork.

In another aspect, a medical system includes a robotic arm, an instrument coupled to the robotic arm. The instrument includes a shaft, a wrist coupled to the shaft, and an end effector configured to generate heat to perform at least two different functions, and a processor configured to modulate a temperature of the end effector to enable two different functions to be performed.

In another aspect, the instrument includes a combined tissue sealer and cutter. The end effector may include a first jaw and a second jaw, wherein at least one of the first jaw and the second jaw may be coupled to a conductive line. The conductive line may be coated with a ferromagnetic coating. The processor may modulate the temperature of the conductive line to enable both sealing and cutting functions.

In another aspect, the end effector includes a first jaw and a second jaw, wherein at least one of the first jaw and the second jaw may be coupled to a conductive pad. The conductive pad may be coated with a ferromagnetic coating. The processor may modulate the temperature of the conductive pad to enable both sealing and cutting functions.

In another aspect, a medical method includes operating a multi-functional instrument to perform a first heat-generating function. The instrument includes a shaft, a wrist having movement in two or more directions, and an end effector including a conductive member for performing the first heat-generating function. The medical method further includes modifying the instrument to perform a second heat-generating function that is different from the first heat-generating function, wherein the second heat-generating function is performed by the conductive member. The first heat-generating function may include sealing and the second heat-generating function may include cutting. The first heat-generating function may be maintained within a first temperature range and the second heat-generating function may be maintained within a second temperature range.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 25 illustrates an alternative embodiment of a medical instrument heated via resistive heating.

FIG. 26 illustrates a side perspective view of one of the jaws of the instrument of FIG. 25.

FIG. 53 illustrates a front perspective view of the medical instrument of FIG. 52 with one of the jaws removed.

FIG. 54 illustrates a front perspective view of the medical instrument of FIG. 52 with one of the jaws removed and the other jaw exposed.

FIG. 55 illustrates a side view of the medical instrument of FIG. 52 with one of the jaws removed.

FIG. 56 illustrates a side view of the medical instrument of FIG. 52 with one of the jaws removed and the other jaw exposed.

FIG. 58 illustrates a side view of the medical instrument of FIG. 57.

FIG. 59 illustrates a side view of the medical instrument of FIG. 57 in an articulated configuration.

FIG. 60 illustrates an alternative embodiment of a medical instrument in a closed configuration including one or more flexures for thermal transfer and cooling.

FIG. 61 illustrates a front view of the medical instrument of FIG. 60 in an open configuration.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
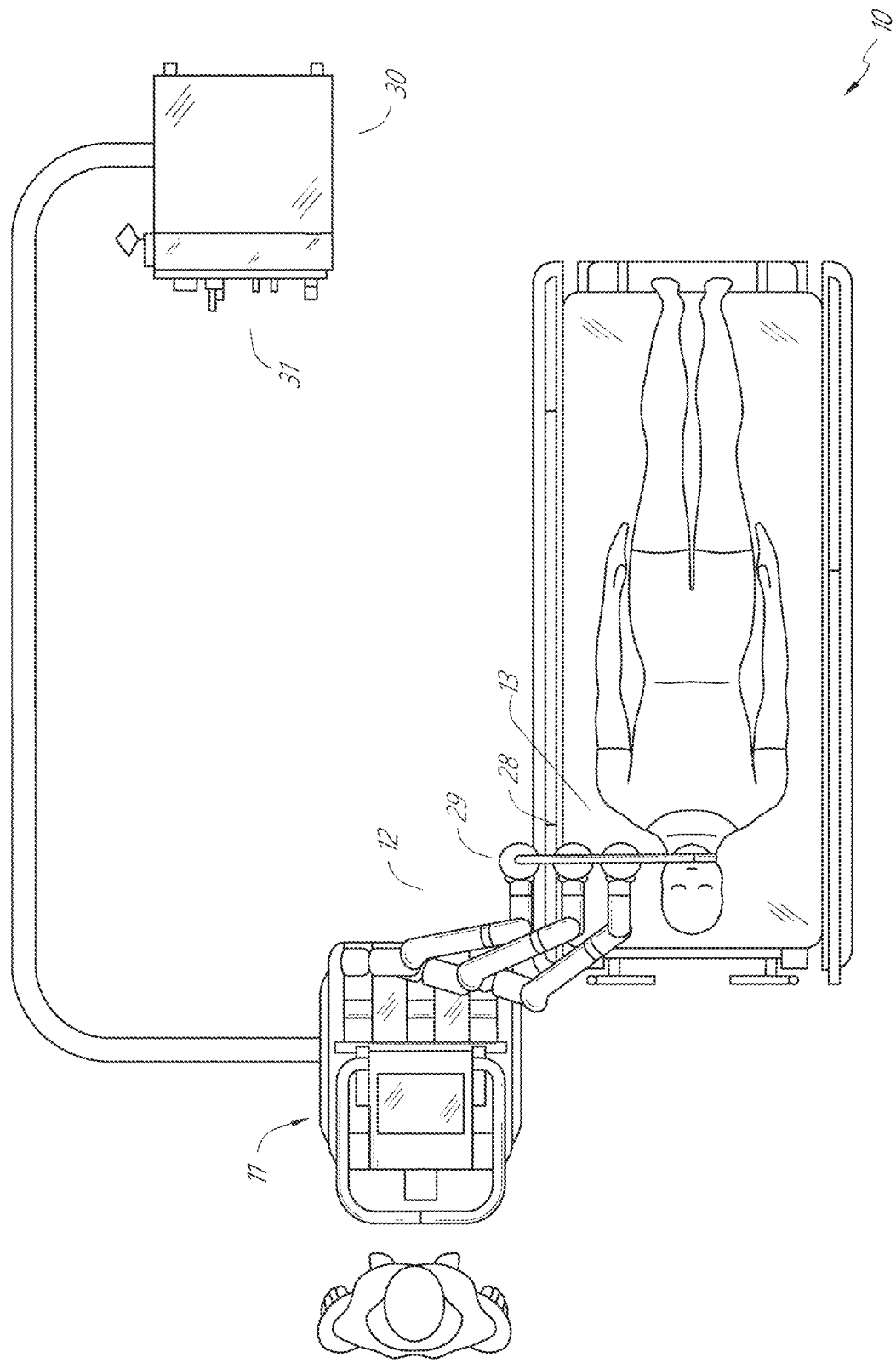
FIG. 1 illustrates an embodiment of a cart-based robotic system arranged for diagnostic and/or therapeutic bronchoscopy procedure(s).
Figure 2:
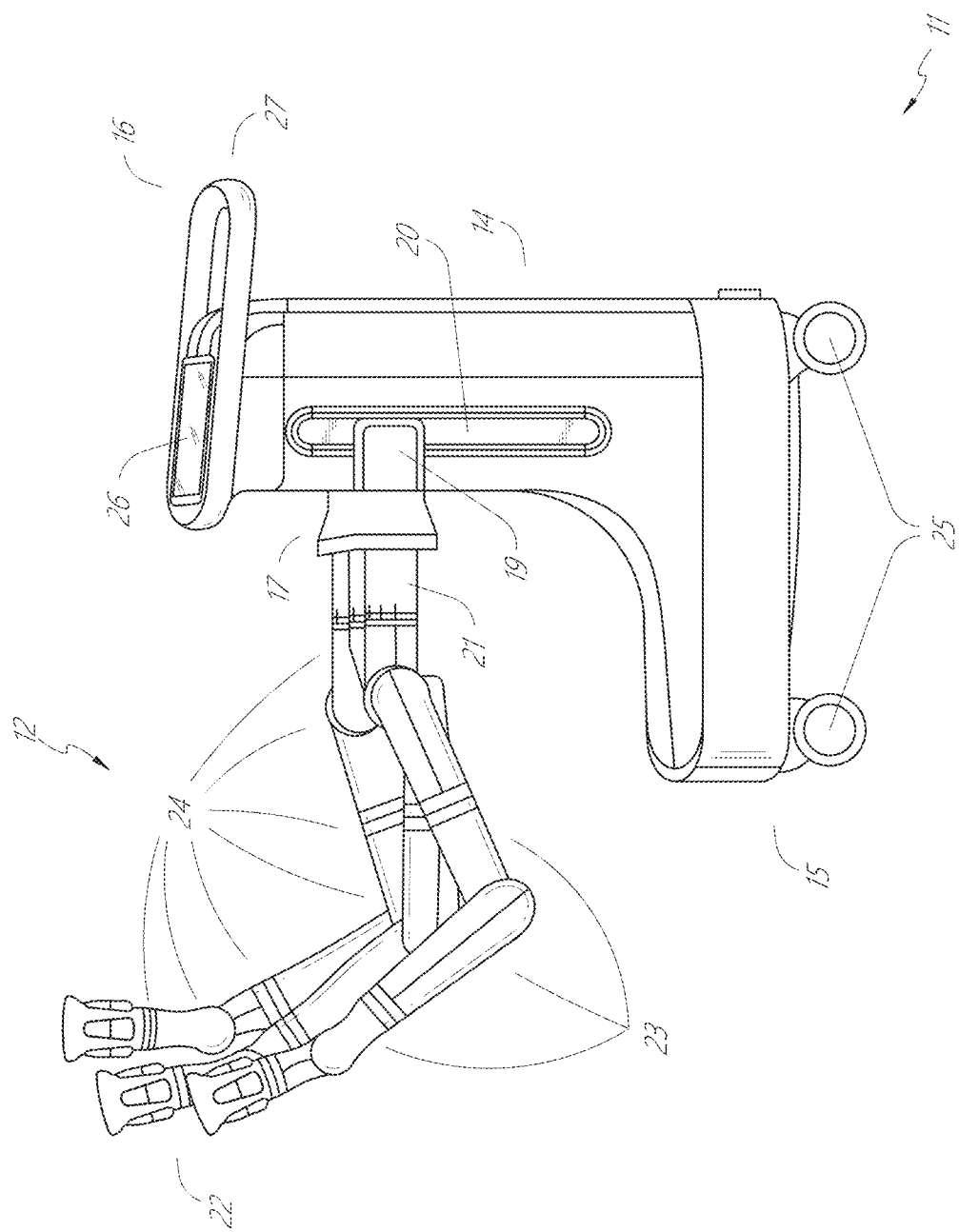
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
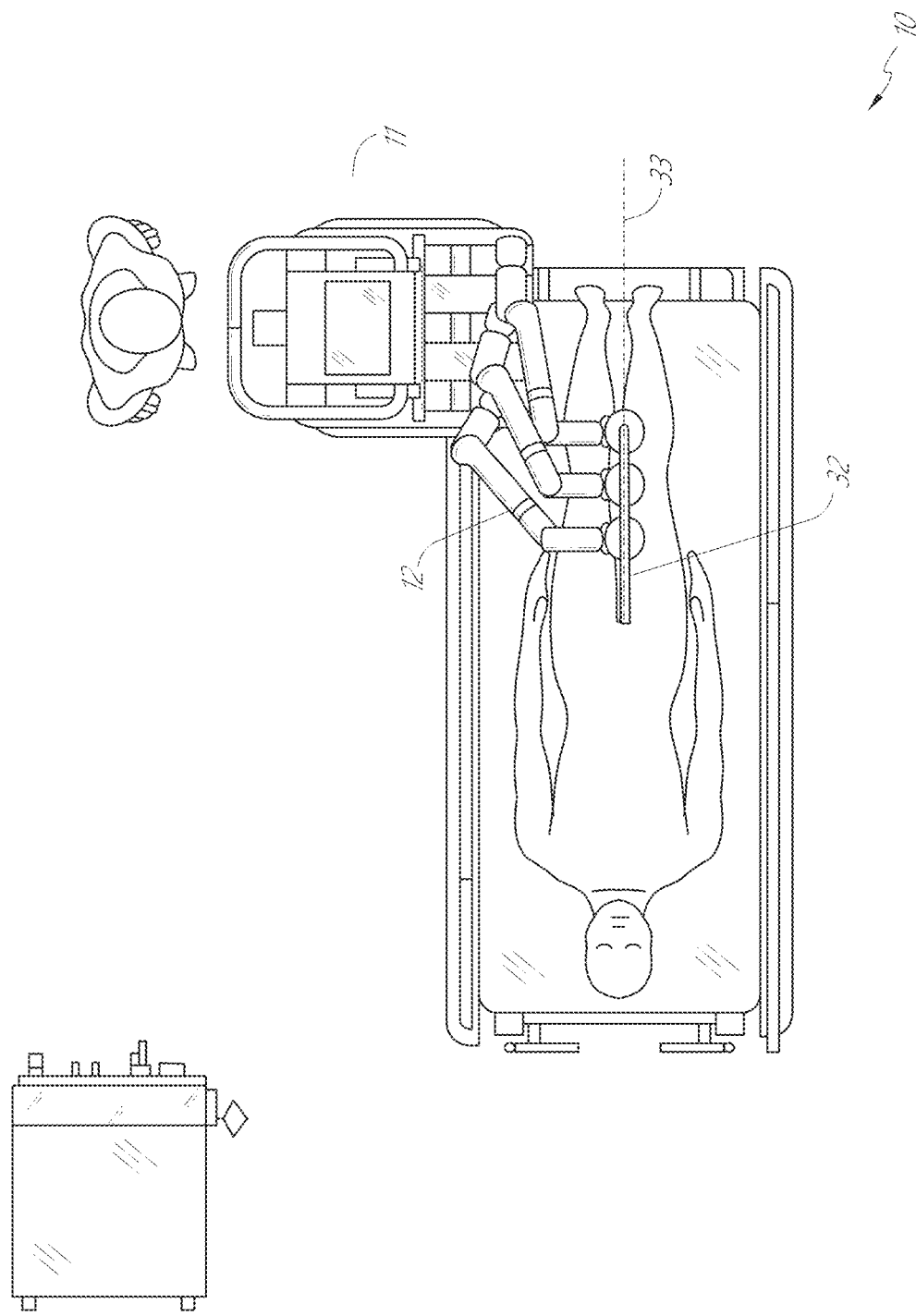
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
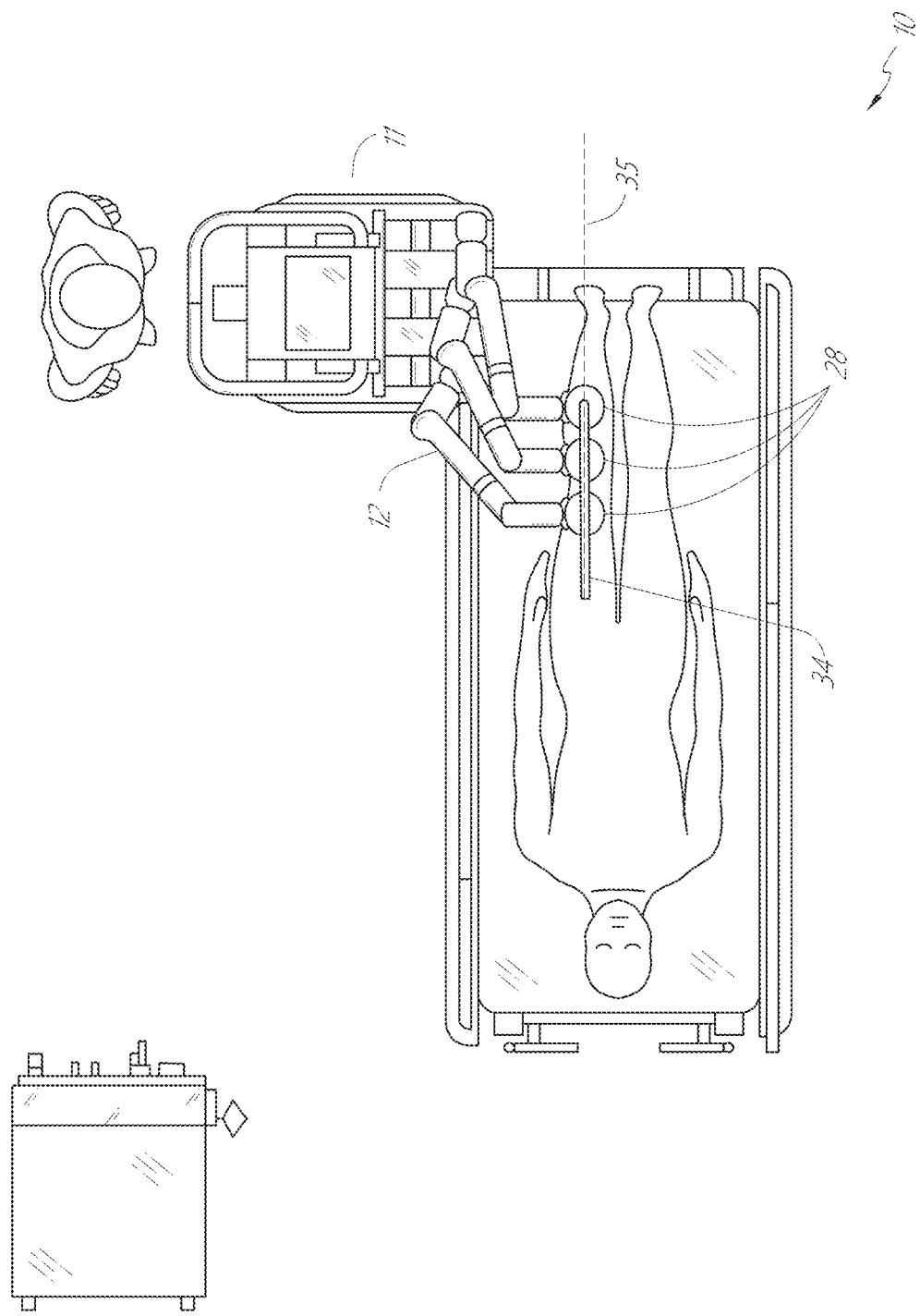
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
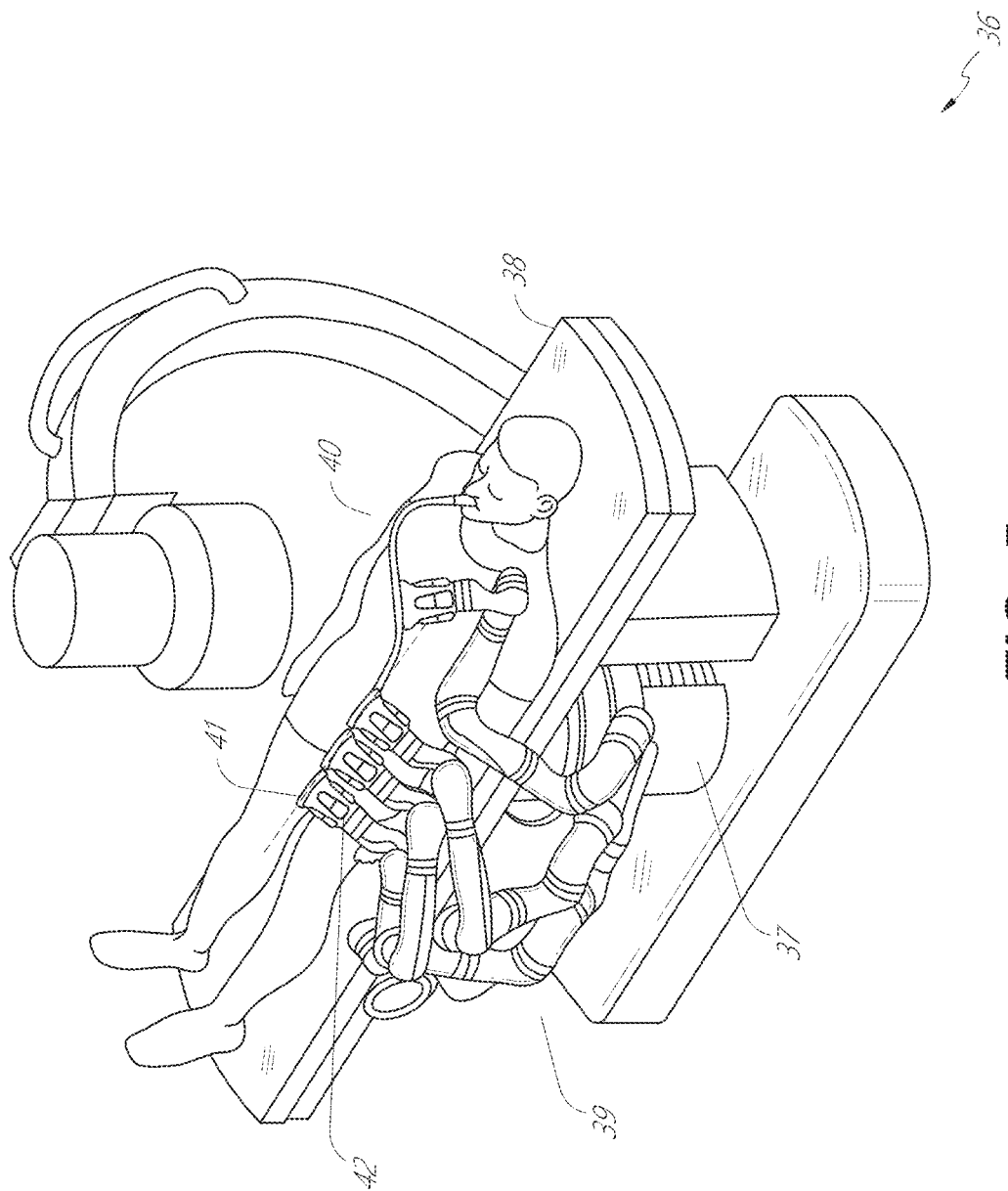
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
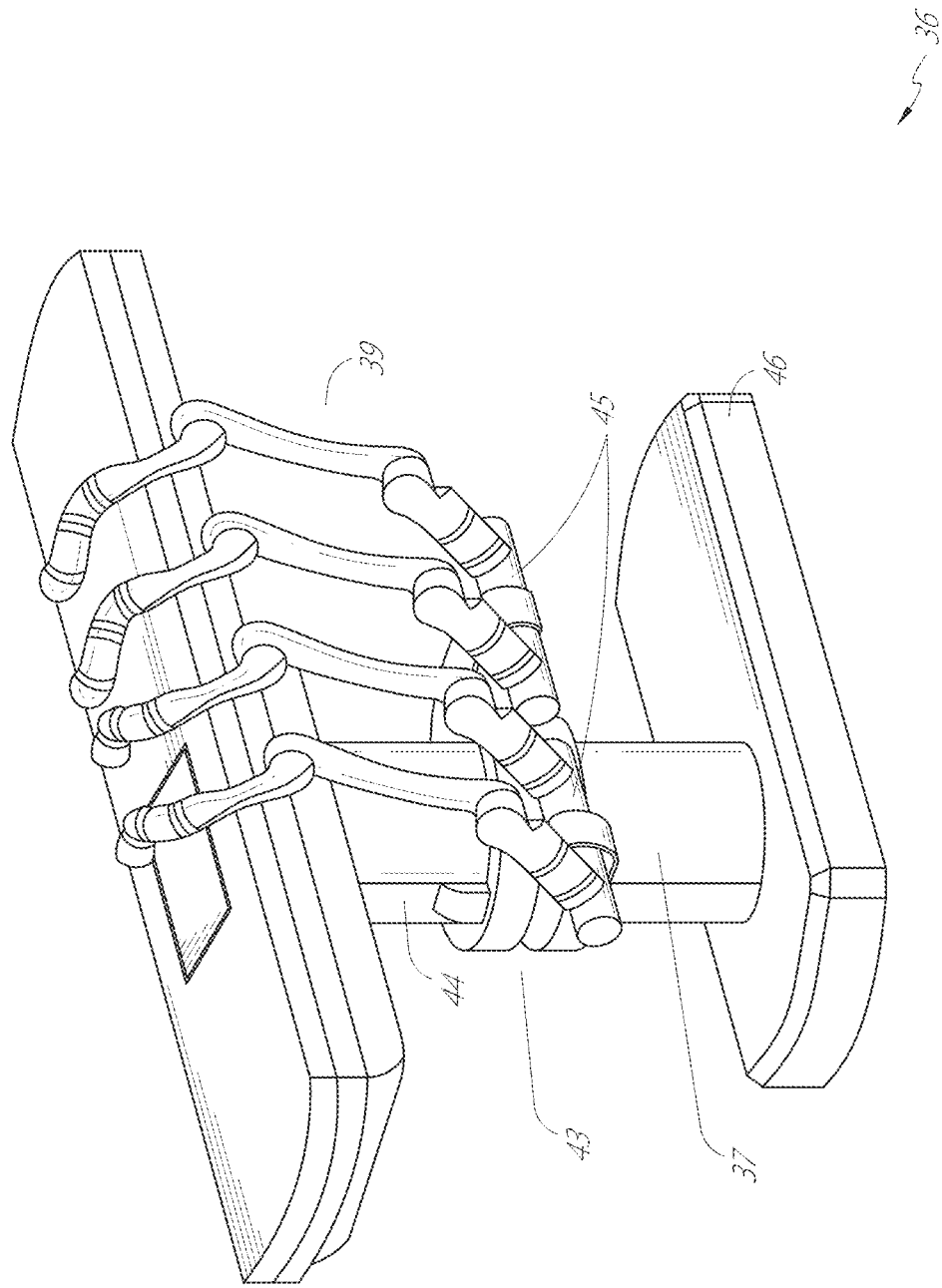
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
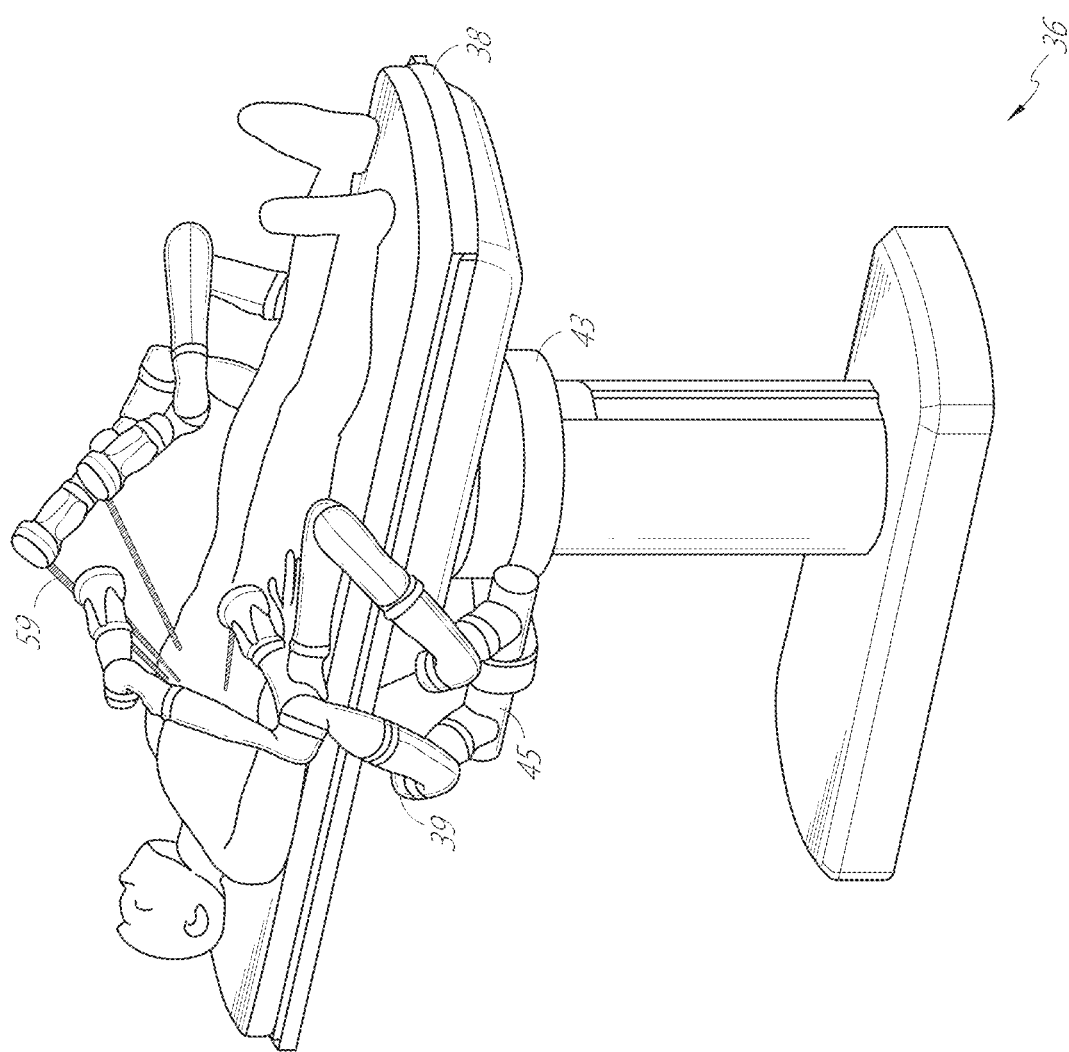
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
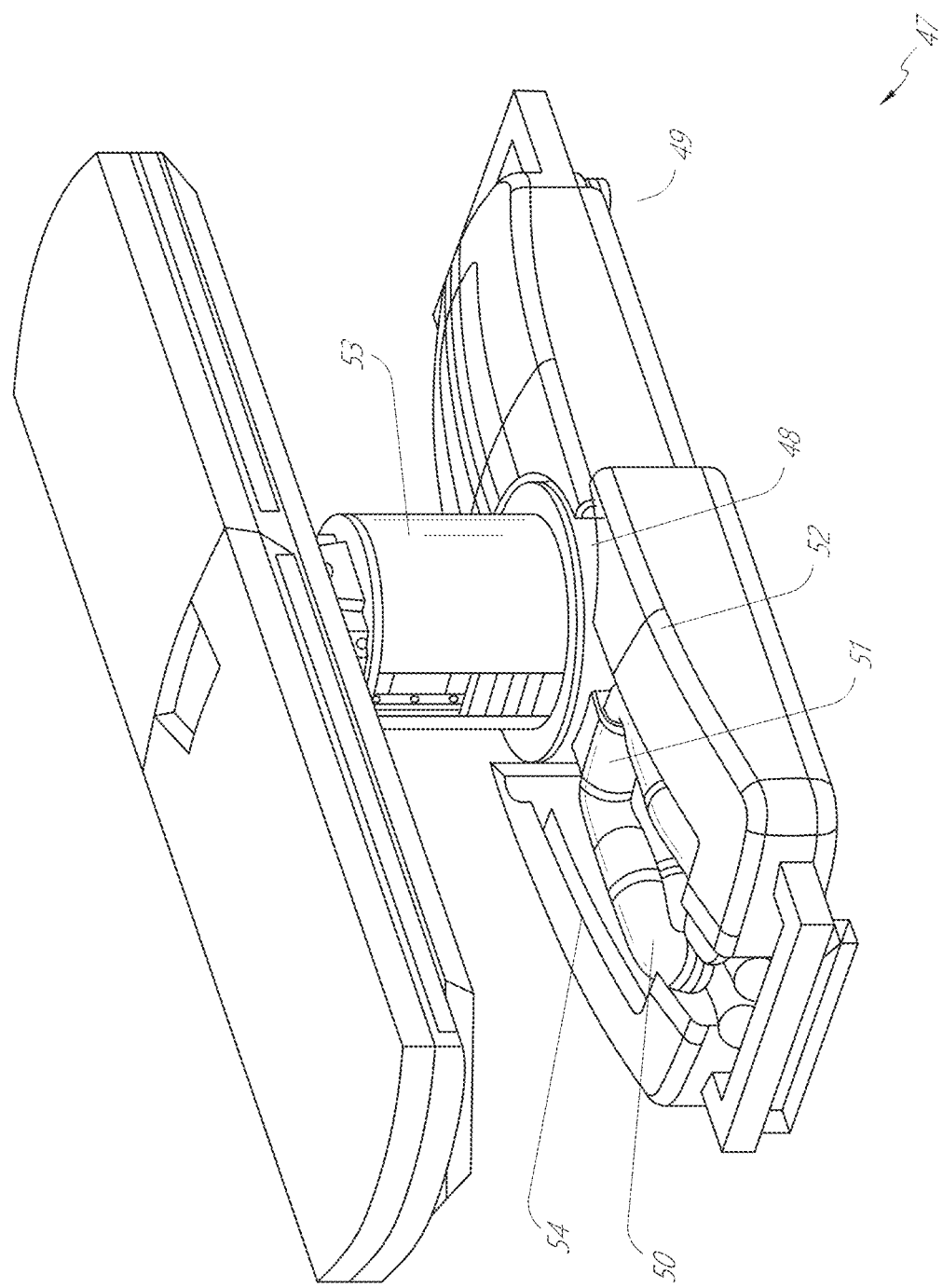
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
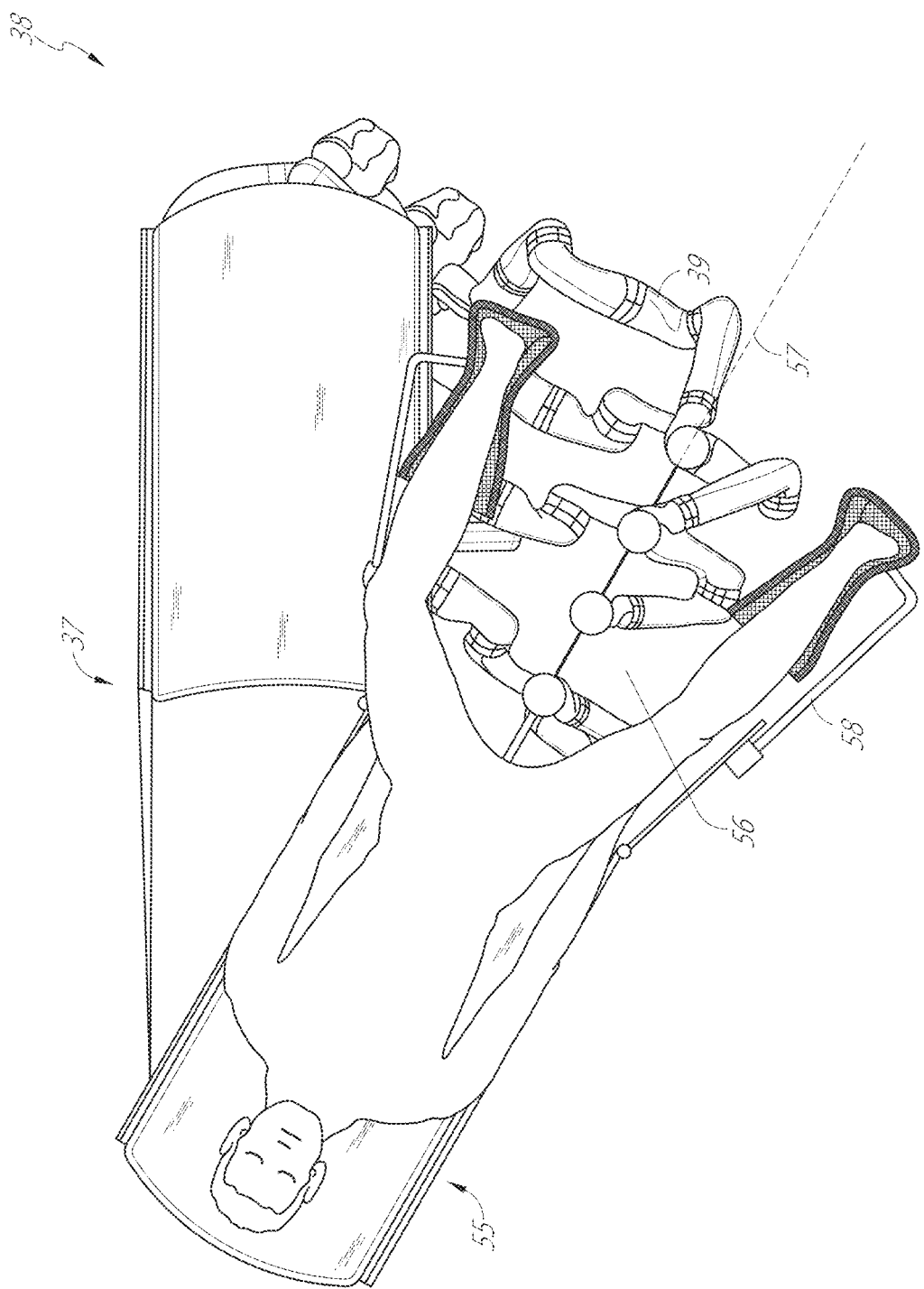
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
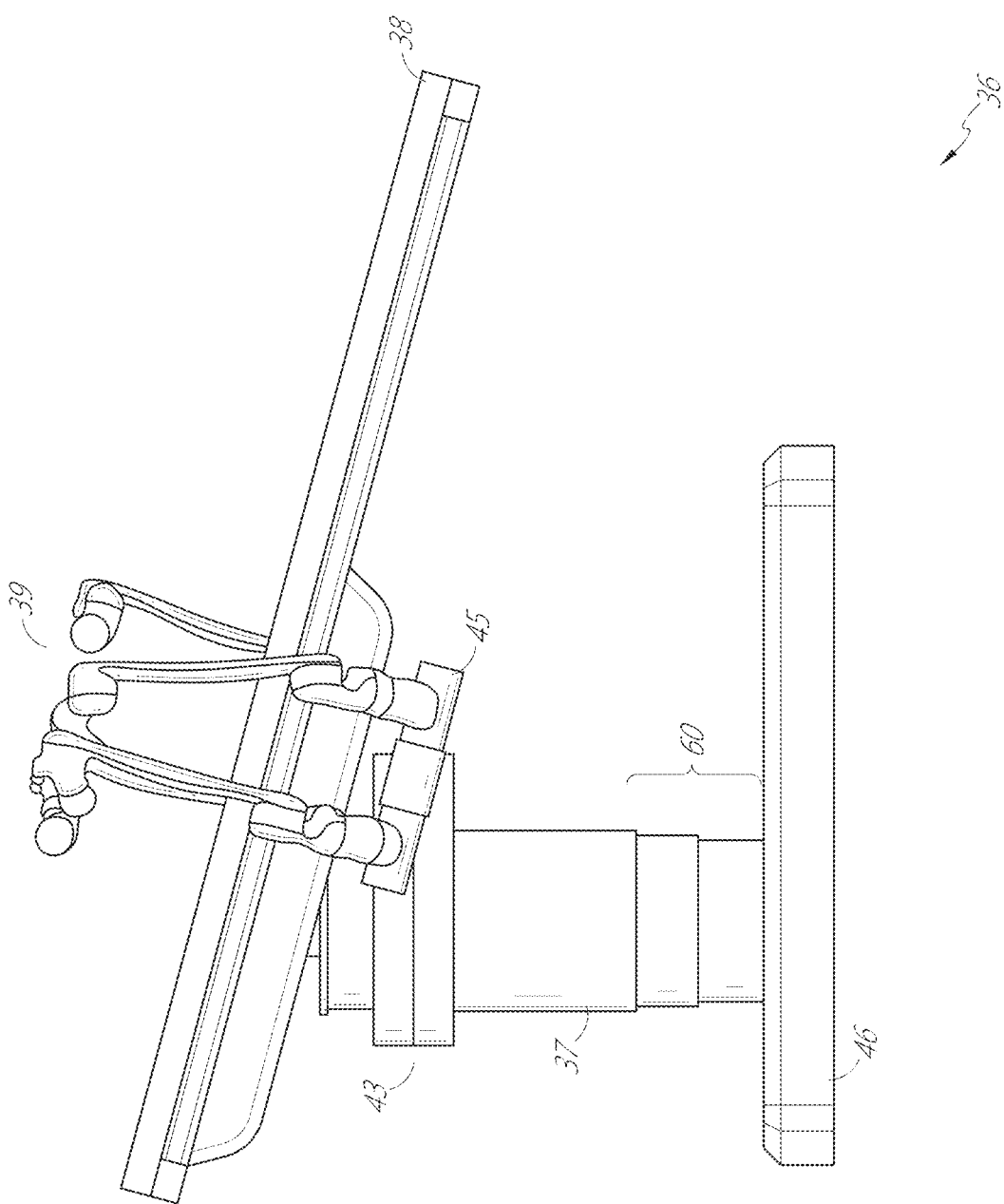
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
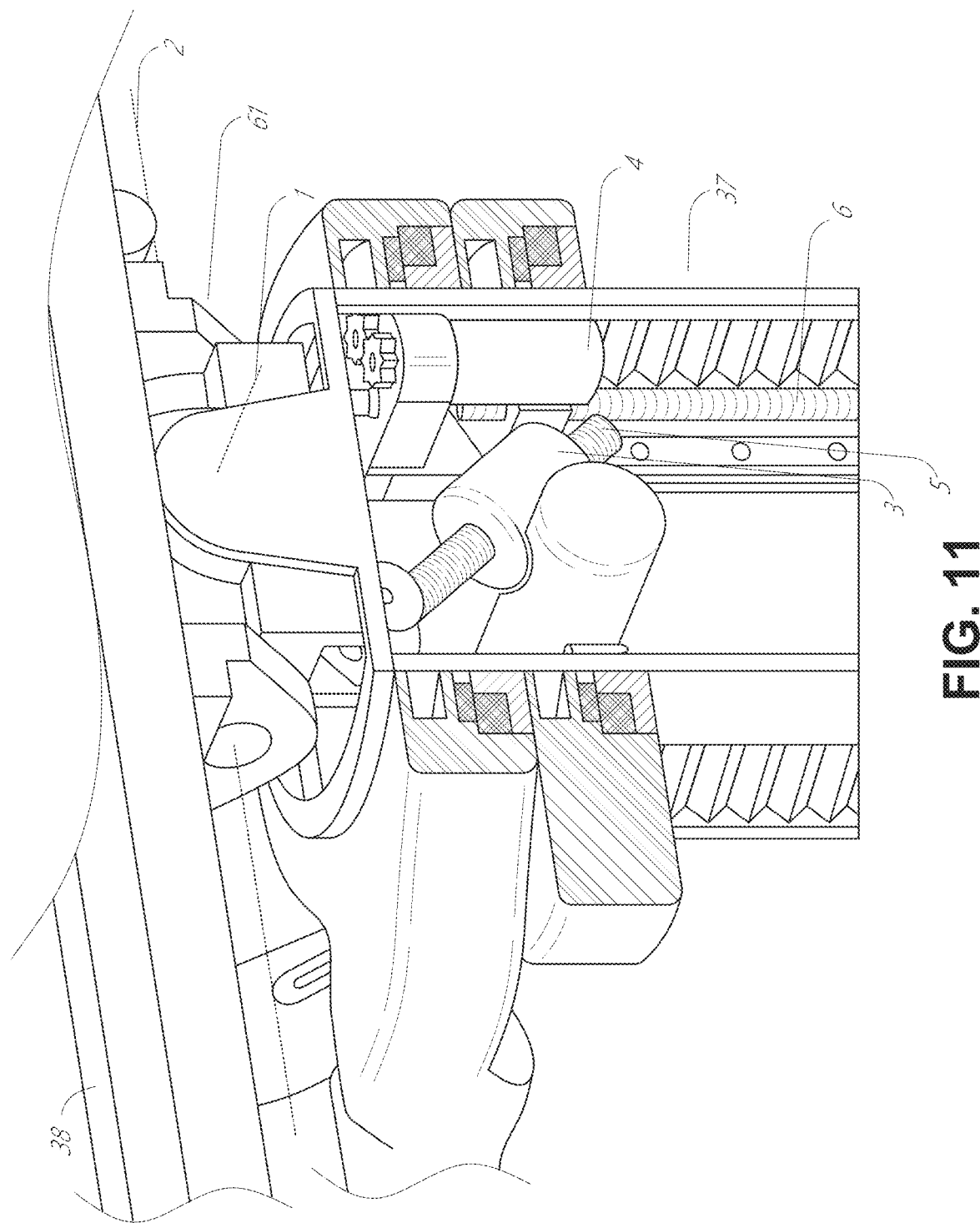
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
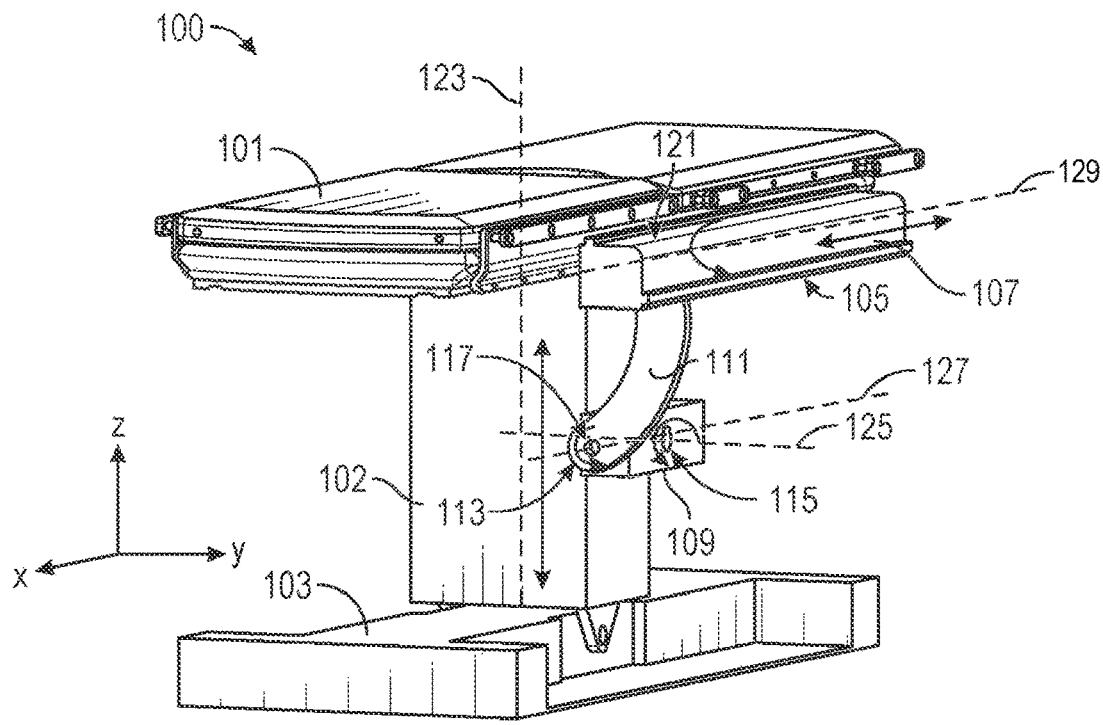
FIG. 12 illustrates an alternative embodiment of a table-based robotic system.
Figure 13:
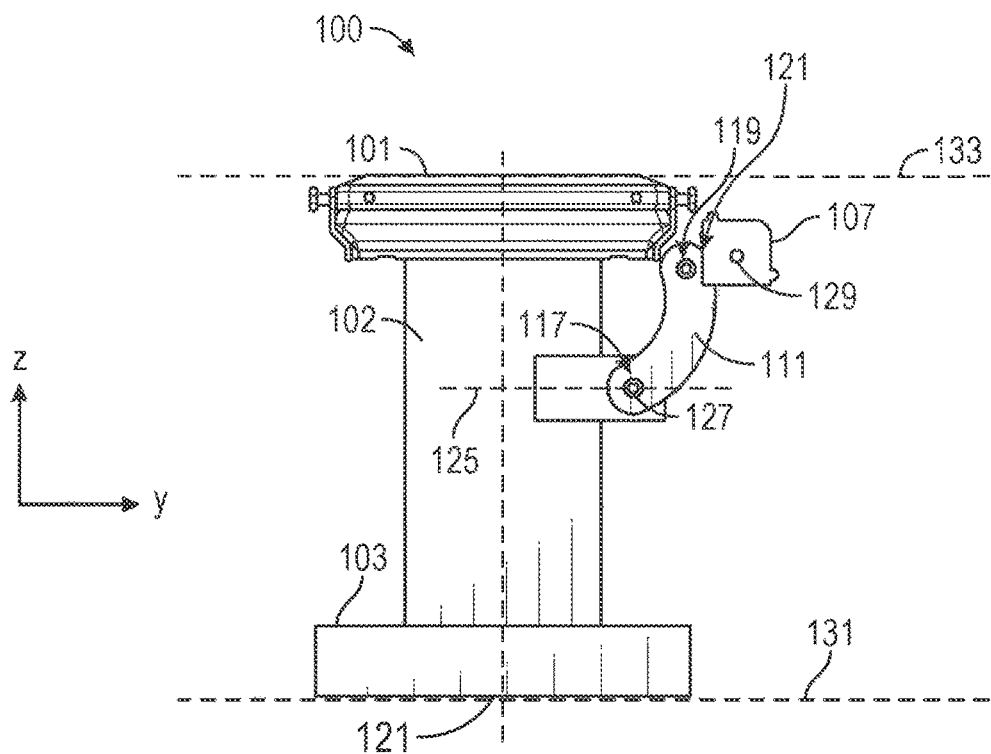
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
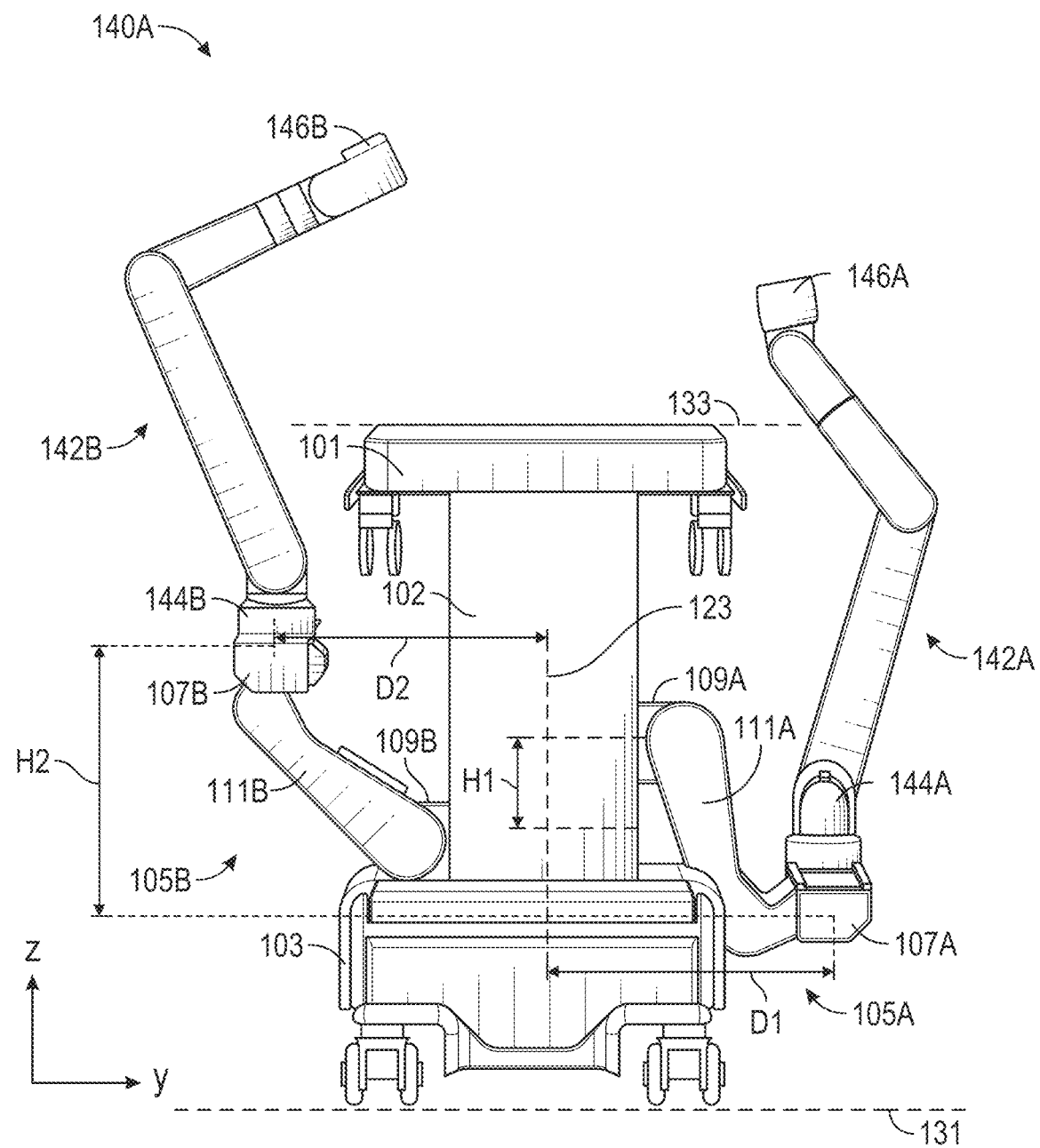
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
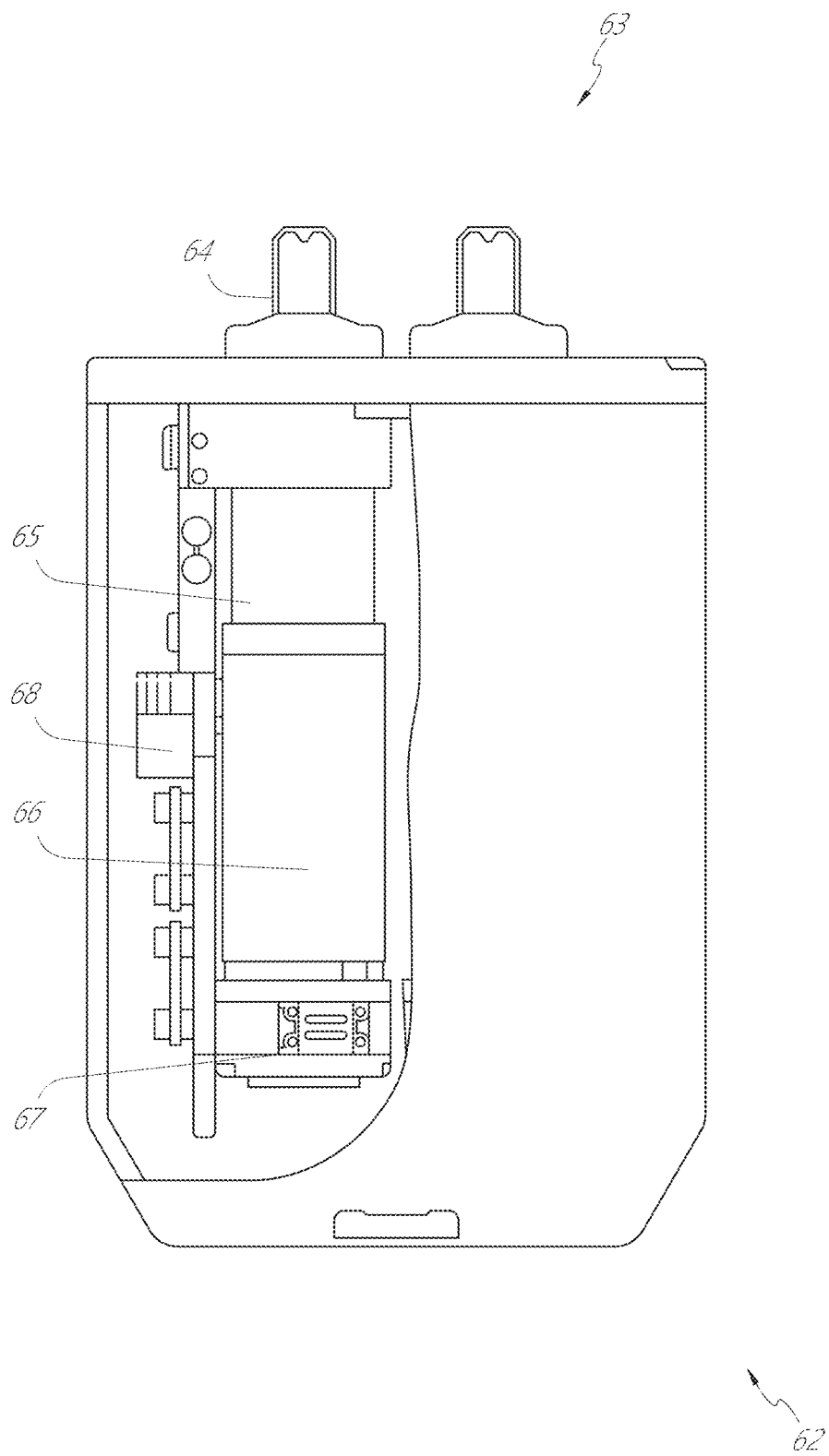
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
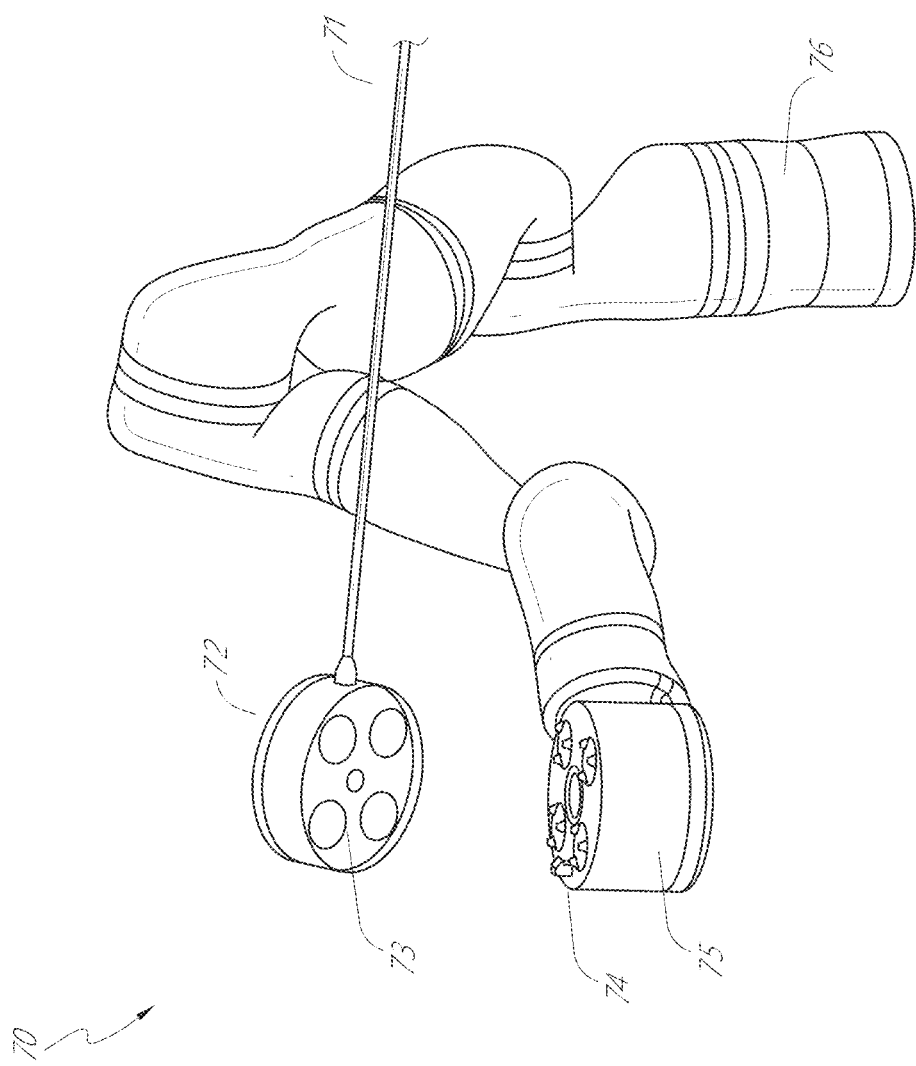
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
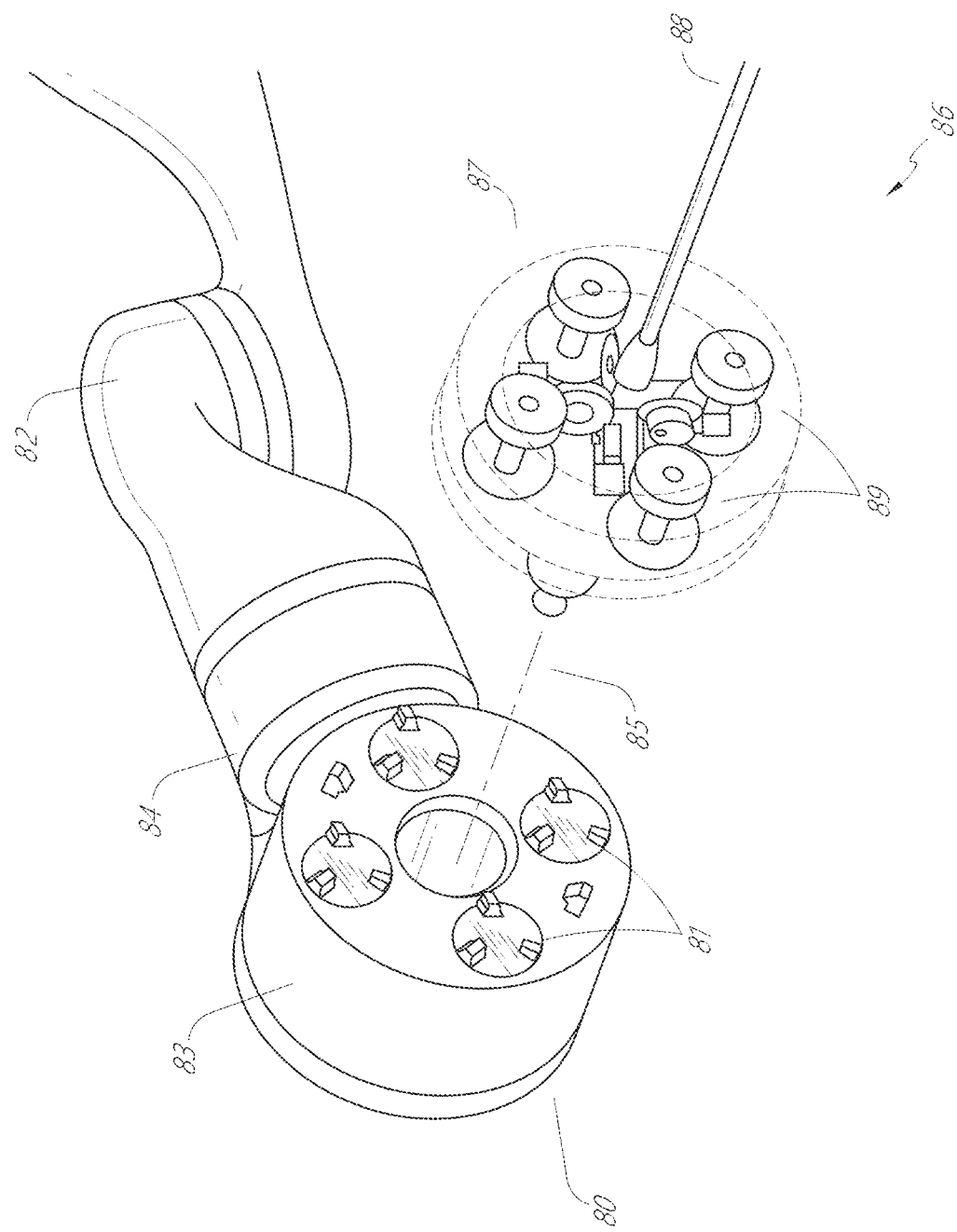
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
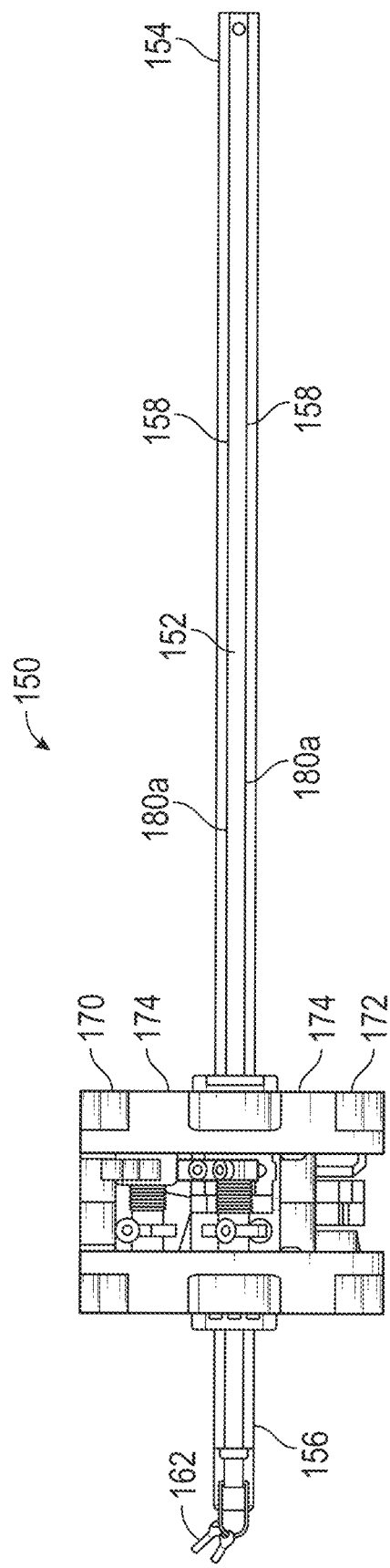
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
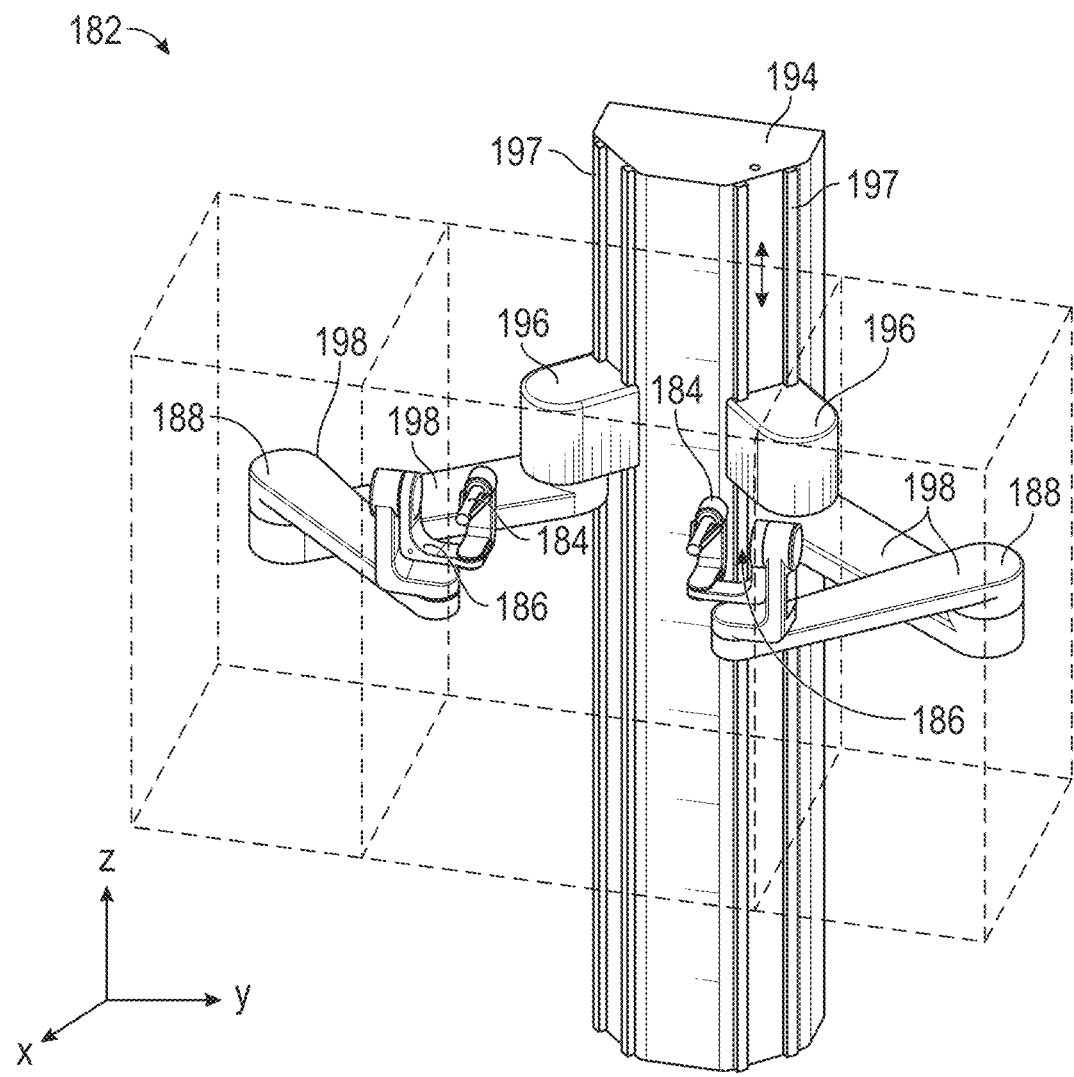
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
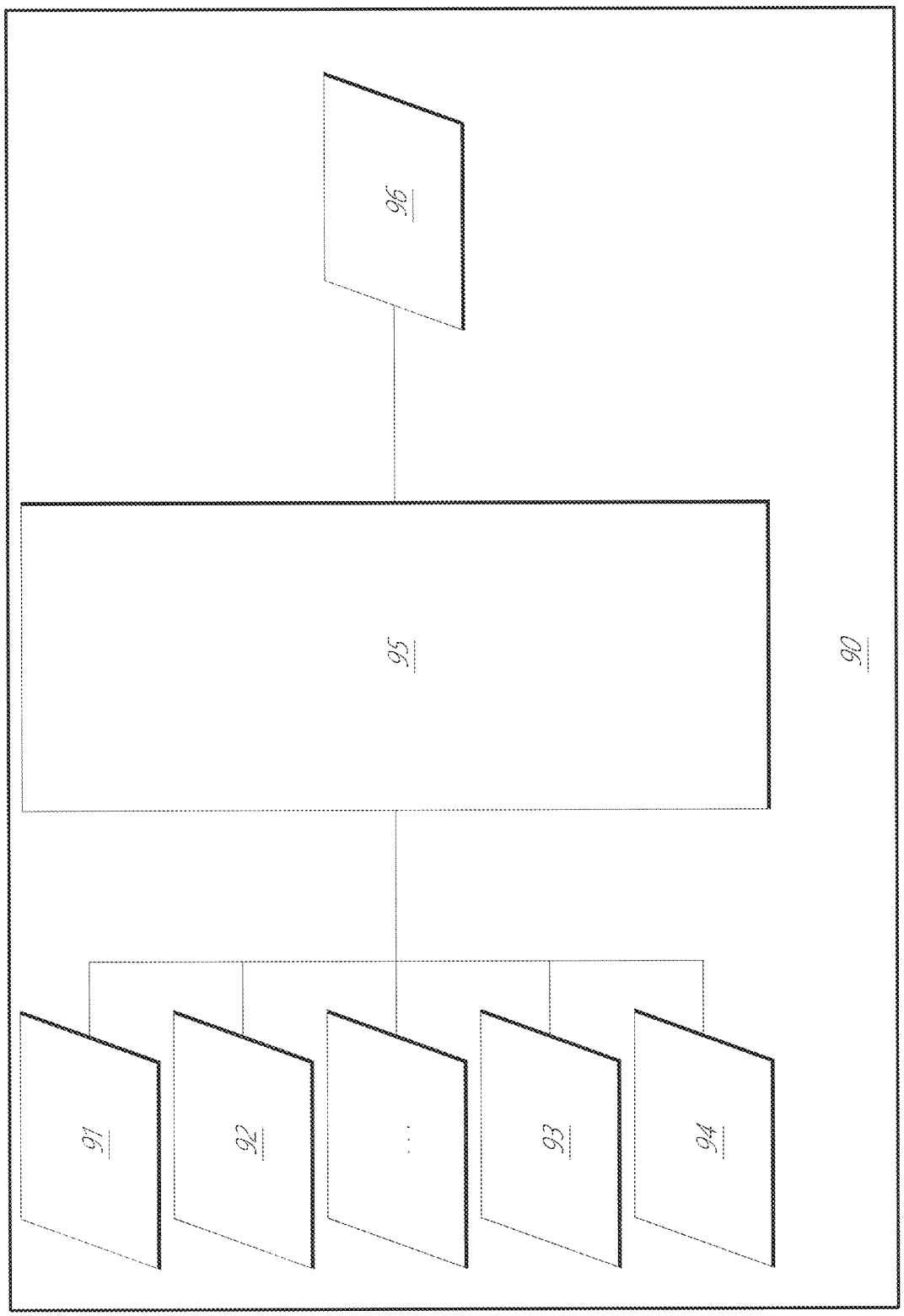
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Instruments for Tissue Sealing and Cutting

This application relates to multi-functional instruments that can be used in various types of surgery, including but not limited to laparoscopic, full open, mini-open and minimally invasive surgeries. In some embodiments, the multi-functional instrument can serve as both a tissue/vessel sealer and a cutter. The tissue sealer works by using grips/jaws to clamp down on tissue with high pressure to stop blood flow in blood vessels and tissue bundles. Energy is then passed through the jaws to heat the tissue so that the molecular bonds of the vessel walls join and fuse the vessel closed. A cutting means is then used to transect the vessel. The present application describes different embodiments of a multi-functional instrument that serve as both a tissue sealer and a cutter with novel cutting mechanisms. In some embodiments, the multi-functional instrument is capable of delivering energy to perform one or more of the following functions, including sealing, hemostasis, cauterization, and cutting.

Advantageously, many of the tissue sealer and cutter embodiments work without a sharp cutting blade to perform cutting, thereby reducing the risk of inadvertent damage to a patient or physician handling the instrument and allowing for ease of reuse. In addition, by not including a sharp cutting blade, it can be easier to reuse instruments, as cutting blades often need to be replaced following one or more repeated uses.

Figure 21:
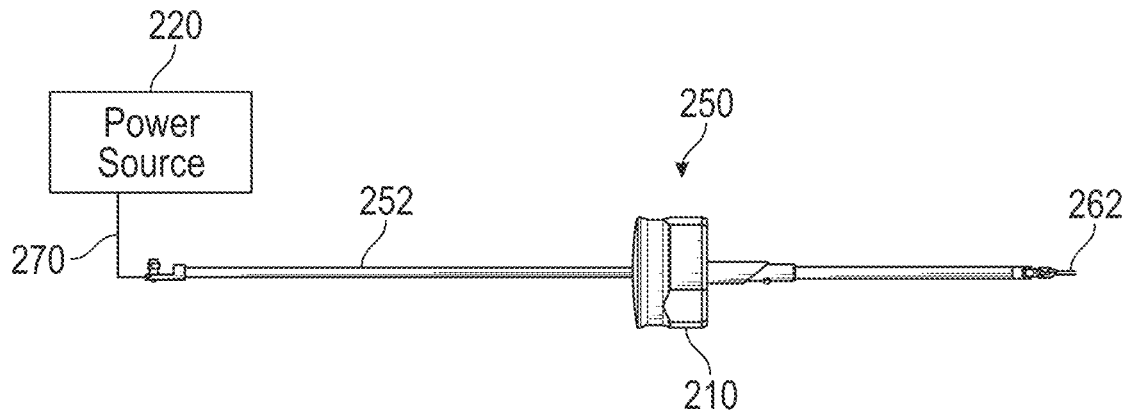
FIG. 21 illustrates a robotically controlled medical instrument coupled to a power source.

FIG. 21 illustrates a robotically controlled medical instrument 250 coupled to a power source 220. The medical instrument 250 can perform multiple functions, including sealing, hemostasis, cauterization and cutting. The medical instrument 250 comprises an elongated shaft 252 coupled to an end effector 262 (e.g., a grasping and cutting mechanism). The medical instrument 250 further comprises a handle 210 that is capable of attaching to a drive mechanism of a robotic arm (such as shown in FIGS. 16 and 17).

In some embodiments, the medical instrument 250 can comprise a vessel/tissue sealer and cutter. As shown in FIG. 21, the medical instrument 250 is coupled to a power source 220 for delivering energy to the end effector 262 of the medical instrument 250. For example, in some embodiments, the power source 220 can be used to deliver current to the end effector 262 to generate heat to perform one or more of sealing, hemostasis, cauterization and/or cutting. As described in further detail below, the medical instrument 250 can comprise an end effector 262 including a pair of grips or jaws capable of gripping and cauterizing tissue. Portions of the end effector 262, including the jaws, can be heated via various mechanisms, as described below. For example, in one embodiment, at least a portion of the end effector 262 can include or be coated with a ferromagnetic material, such that current delivered through the end effector 262 can generate resistive heat.

For the tissue sealer and cutter, different functions can be performed at different temperatures. For example, a cutting function may be performed at a higher temperature (e.g., between 210 and 410 degrees Celsius) than a sealing function (e.g., between 70 and 210 degrees Celsius). As such, in order to generate the appropriate amount of heat at the end effector 262, the end effector 262 can include one or more sensors for detecting temperature. Furthermore, the power source 220 can include a built-in power adjuster so that heat can be easily controlled. The power source 220 is capable of adjusting the current (e.g., high frequency alternating currents) to accommodate different functions of the medical instrument 250.

In some embodiments, the power source 220 and accompanying power adjuster can be advantageously connected to a robotic processor such that the amount of heat can be easily controlled. In some embodiments, the processor can include one or more pre-set values for different parameters, such as the level of current that is generated by the power source or the temperature at the distal end of the tissue sealer. Should an actual reading deviate from these pre-set values, the processor can automatically adjust the power source via the power adjuster. For example, the processor can be pre-programmed such that cutting occurs between 210 and 410 degrees Celsius, while sealing occurs between 70 and 210 degrees Celsius. Should a user desire a cutting function, the robotic processor can help to ensure that the tissue sealer stays between the 210 and 410 degrees Celsius range. If the tissue sealer is detected out of this temperature range, the power source can be automatically adjusted to reduce the amount of generated heat. The use of a processor to control temperature is a great improvement over tissue sealers that are capable of just manual temperature adjustment. In some embodiments, the tissue sealer can have its temperature controlled both via a processor and manually.

Figure 22:
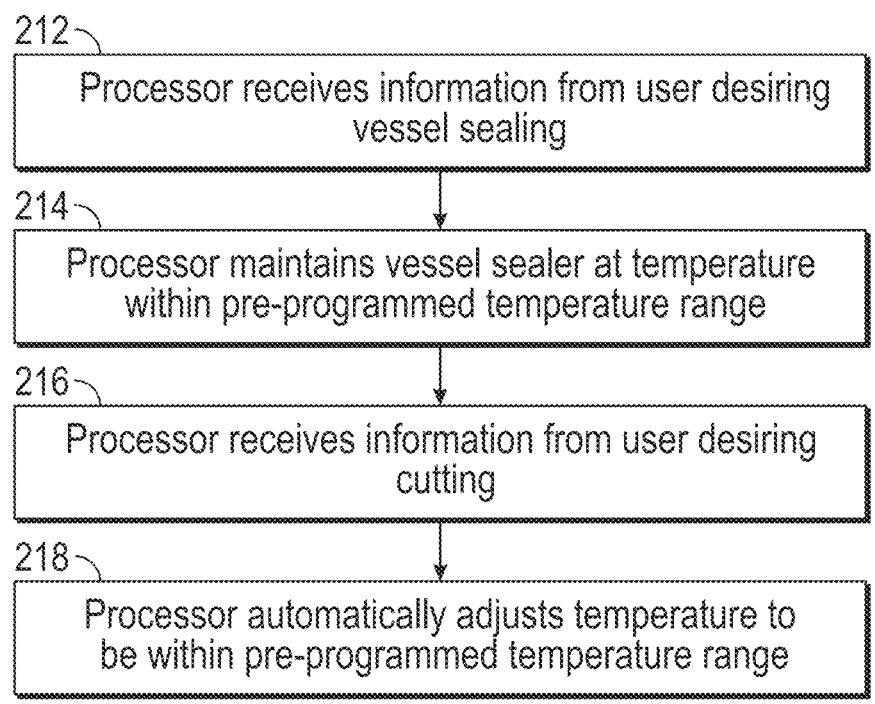
FIG. 22 illustrates a flow chart for a method of temperature modulation utilizing a processor.

FIG. 22 illustrates a flow chart for a method of temperature modulation utilizing a processor. In this method, a processor receives information from a user desiring vessel sealing 212. Based on these instructions, the processor maintains the vessel/tissue sealer at a temperature within a pre-programmed temperature range 214 for sealing. The processor can also receive information from a user desiring cutting 216. Based on these instructions, the processor can automatically adjust the temperature (e.g., by modulating the power source) to be within a pre-programmed temperature range 218 for cutting.

Any of the instruments described herein can be robotically controlled. In addition, these instruments can be operatively coupled to a processor that automatically controls different parameters, such as temperature, thereby advantageously allowing the instruments to have different functionality.

A. Non-Bladed Instruments with Thermal Capabilities.

Below are different embodiments of multi-functional instruments (e.g., combined tissue grasper and cutter) that are capable of generating heat via various thermal mechanisms, including resistive, inductive and/or RF modalities. In some embodiments, these instruments include distal end effectors that are coupled to a multi-degree of freedom (DOF) wrist. Though instruments that have multi-DOF wrists provide a number of challenges, including the challenge of being able to fit one or more articulating and conducting cables through the wrist and to the end effector, these instruments have novel architectures with novel cable paths that enable multi-functional use. One skilled in the art will appreciate that any of the end effectors described herein can be used with any of the multi-DOF wrist architectures described herein.

i. Magnetic Induction

Figure 23:
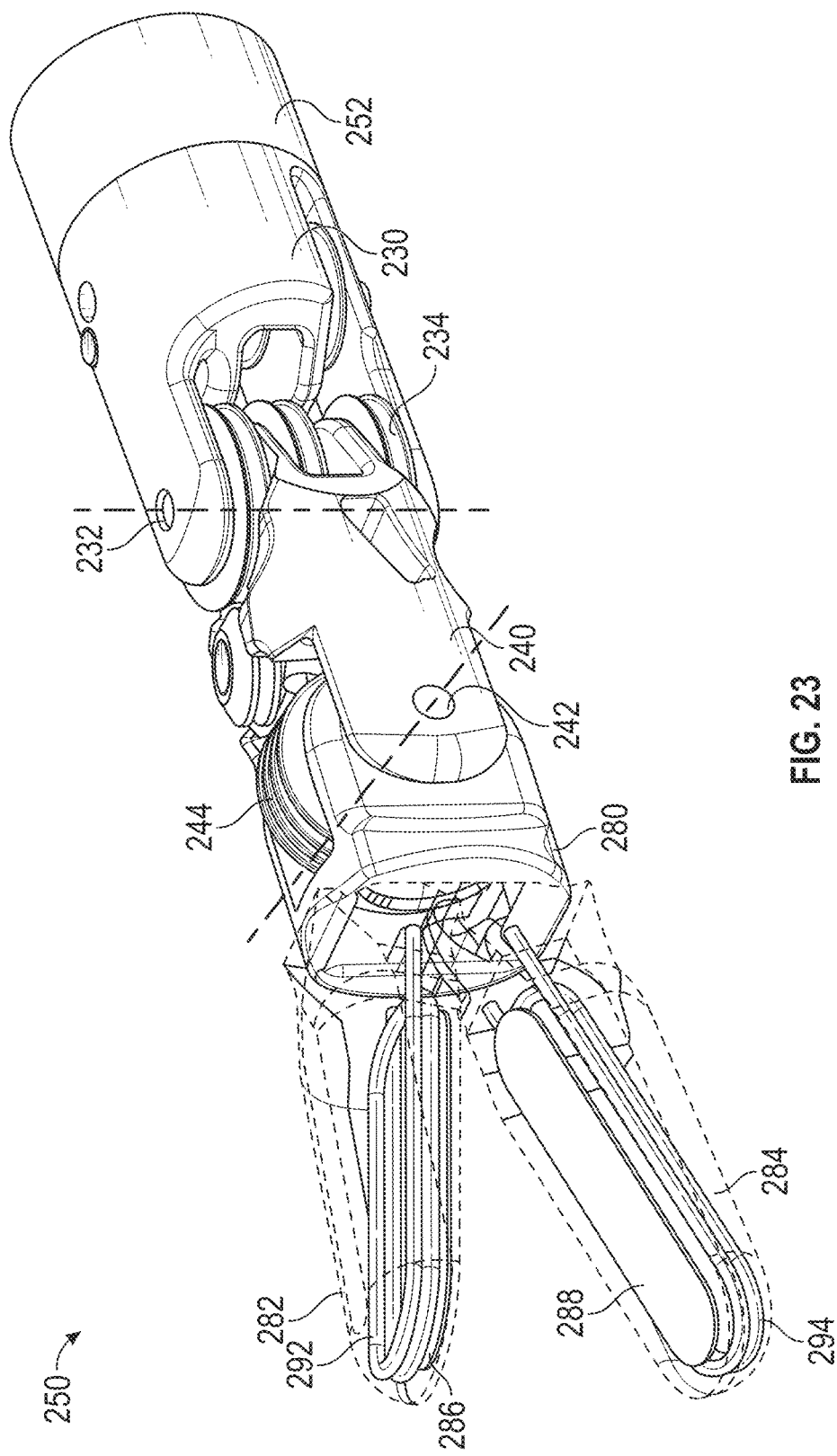
FIG. 23 illustrates a top perspective view of a distal portion of a medical instrument that is capable of resistive heating.

FIG. 23 illustrates a top perspective view of a distal portion of a medical instrument 250 that is capable of resistive heating. The medical instrument 250 comprises a multi-functional grasper and cutter comprised of a shaft 252, a wrist comprising a proximal clevis 230 and a distal clevis 240, and an end effector including an upper jaw 282 and a lower jaw 284. At least one of the upper jaw 282 and lower jaw 284 includes a pad (e.g., upper pad 286, lower pad 288) formed in part of a ferrous material that allows resistive heat to be generated. In this embodiment, the instrument 250 is capable of multiple functions, including sealing and cutting, simply by modifying the temperature of the upper and lower pads 286, 288, thereby advantageously reducing the need for a physical cutting blade. In an alternative embodiment, a physical cutting blade (not shown) can also be provided with the upper and lower pads 286, 288 if desired.

The elongated shaft 252 can be coupled to an instrument handle 270, as shown best in FIG. 21. In some embodiments, the elongated shaft 252 is capable of translating relative to the instrument handle 270, thereby providing movement along an insertion axis.

The wrist is comprised of a proximal clevis 230 and a distal clevis 240 that allow the wrist to move in multi-degrees of freedom. For example, in the present embodiment, the wrist is capable of moving in both pitch and yaw. A pin joint 232 extends through openings in the proximal clevis 230 and extends along a pitch axis. Similarly, a pin joint 242 extends through openings in the distal clevis 240 and extends along a yaw axis. One or more pulleys 234 are received within the proximal clevis 230. Similarly, one or more pulleys 244 are received within the distal clevis 240. Robotically controlled cables or cable segments are designed to extend through the one or more pulleys 234, 244 to thereby cause articulation of the instrument in pitch and yaw. The distal clevis 240 also receives a base or housing 280 for receiving the proximal clevis 230 and distal clevis 240 therein.

The end effector comprises an upper jaw 282 and a lower jaw 284 for grasping tissue. The upper jaw 282 comprises an upper pad 286 and a conductive line 292 adjacent to the upper pad 286. Likewise, the lower jaw 284 comprises a lower pad 288 and a conductive line 294 adjacent to the lower pad 288. In some embodiments, the upper pad 286 and lower pad 288 can be formed entirely of a ferrous material. In other embodiments, the upper pad 286 and the lower pad 288 can be formed of a non-ferrous material that is coated at least in part by a ferrous material. In some embodiments, the conductive lines 292, 294 can form a loop or coil (as shown in FIG. 23) that extends substantially around a perimeter of the upper and lower pads 286, 288. In other embodiments, the conductive lines 292, 294 are not in the form of a loop or coil, but is simply a straight, linear, wavy, or zig-zagged line that extends adjacent the pads 286, 288.

Current can be delivered through the conductive lines 292, 294 from a power source 220 (as shown in FIG. 21) to generate heat within the upper and lower pads 286, 288. Current is delivered through the conductive lines 292, 294, thereby generating heat in the upper and lower pads 286, 288 via magnetic induction. Advantageously, the heat can be monitored and modulated via a processor, as described above, thereby allowing for different functions, such as cauterization, hemostasis or cutting.

Figure 24:
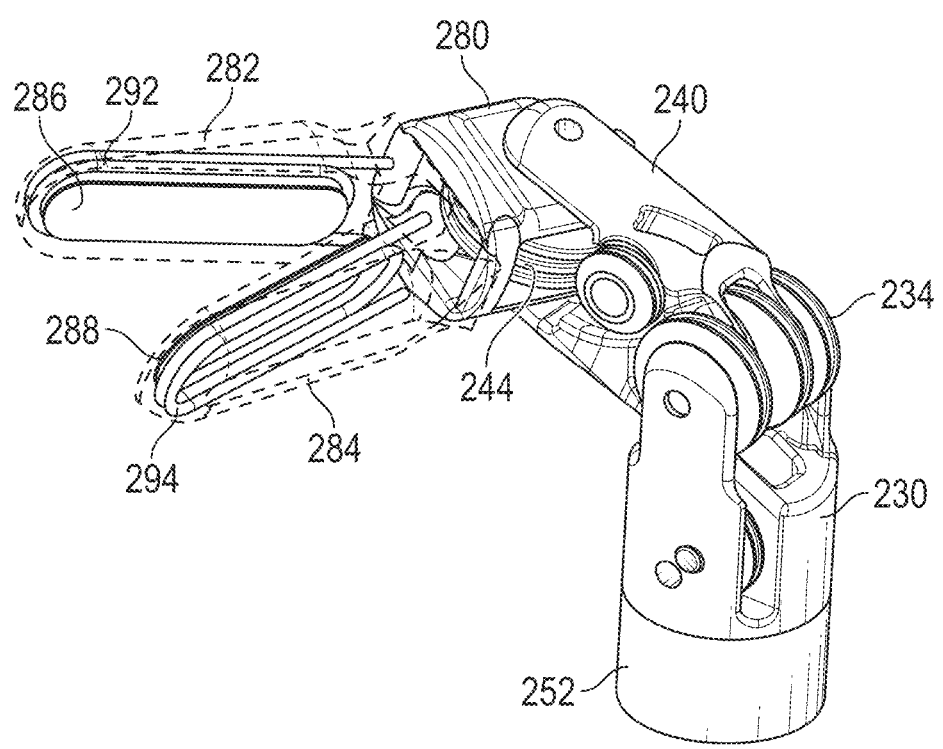
FIG. 24 illustrates the instrument of FIG. 23 in an articulated configuration.

FIG. 24 illustrates the instrument of FIG. 23 in an articulated configuration. From this view, one can see the instrument 250 articulated in both pitch and yaw. Advantageously, the instrument 250 is capable of delivering current to the end effector even when the wrist 250 is articulated in pitch and yaw.

FIG. 25 illustrates an alternative embodiment of a multi-functional medical instrument 350 (e.g., sealer and cutter) heated via resistive heating. In this embodiment, the medical instrument 350 does not utilize a ferromagnetic pad. Rather, the medical instrument 350 is comprised of one or more conductive lines 370 that are coated with a ferromagnetic coating 374. A power source can generate current that will flow through the one or more conductive lines 370. The current will generate heat via the ferromagnetic coating 374 (as shown in FIG. 26).

The medical instrument 350 comprises a pair of jaws 382, 384 coupled to a multi-DOF wrist including a proximal clevis 330 and a distal clevis 340. In the present embodiment, the distal clevis 340 is in the form of a "frankenclevis" that includes two different types of joints on its upper portion and bottom portion. Along its bottom portion, the distal clevis 340 engages with the proximal clevis 330 via an unpinned rolling joint about a pitch axis. As such a rolling joint is unpinned, this advantageously provides room for cables to pass through the wrist. Along its upper portion, the distal clevis 340 comprises a pinned joint 343 about a yaw axis. One or more pulleys 344 are received within the distal clevis 340. Robotically controlled cables or cable segments are designed to extend through the one or more pulleys 344 to thereby cause articulation of the instrument in pitch and yaw.

Figure 27:
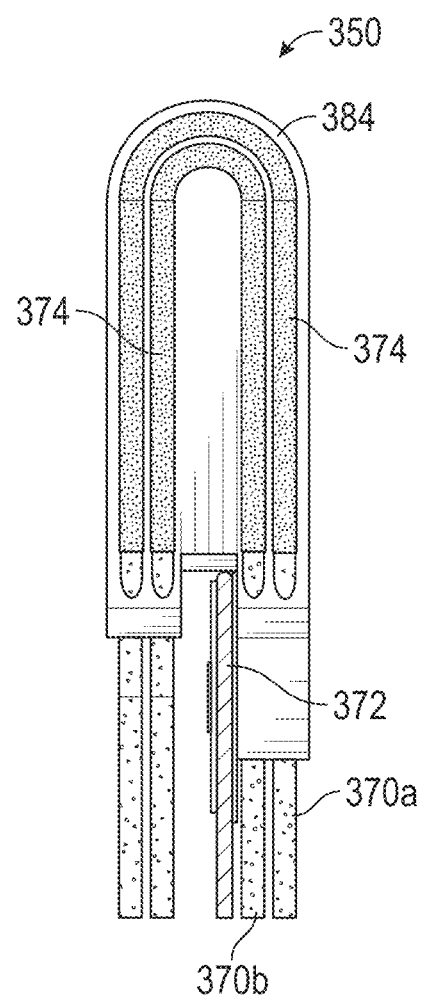
FIG. 27 illustrates a front view of the one jaw of the instrument of FIG. 26.

Various cables extend from a shaft (not shown) and through the wrist. One or more electrical or conductive cables 370 extend through the wrist and into the jaws 382, 384 (as shown in FIGS. 26 and 27). The conductive cables 370 are coated with a ferromagnetic coating 374 to generate resistive heat to perform various functions, including seal-ing, hemostasis, cauterization and cutting. In addition, one or more articulation or drive cables 372 extend through the wrist and into the jaws 382, 384. The drive cables 372 are capable of articulating the wrist in pitch and yaw.

FIG. 26 illustrates a side perspective view of one of the jaws of the instrument of FIG. 25. FIG. 27 illustrates a front view of the one jaw of the instrument of FIG. 26. From these views, one can see the path of the conducive cables 370 as they extend through the jaw 384. The conductive cables 370 advantageously extend about a perimeter of the jaw 384. In some embodiments, the cables 370 comprise an outer cables 370a and inner cables 370b that extend circuitously (e.g., about a loop) of the jaw 384.

Figure 28:
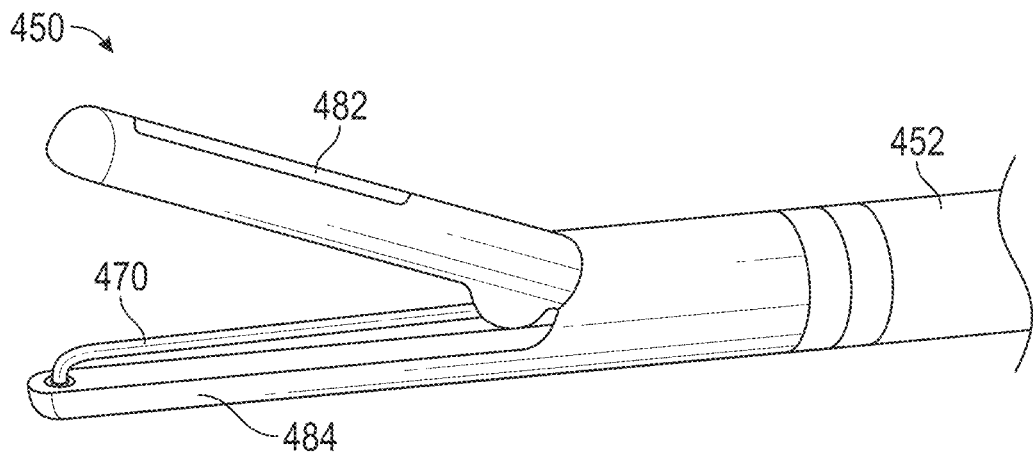
FIG. 28 illustrates an alternative embodiment of a medical instrument heated via resistive heating.

FIG. 28 illustrates an alternative embodiment of a medical instrument heated via resistive heating. In contrast to the embodiment in FIGS. 25-27, in the present embodiment, the medical instrument 450 comprises a multi-functional tissue sealer and cutter having an upper jaw 482 and a lower jaw 484 that includes a single conductive line 470 that extends along a mid-longitudinal axis of one of the jaws. While in the present embodiment the single conductive line 470 is visible only on the bottom jaw 484, in some embodiments, the upper jaw 482 may also include a conductive line.

In FIG. 28, a current has been delivered from a power source through the conductive line 470. The conductive line 470 is advantageously coated with a ferromagnetic coating, thereby allowing for magnetic induction to occur (as shown in FIG. 29).

Figure 29:
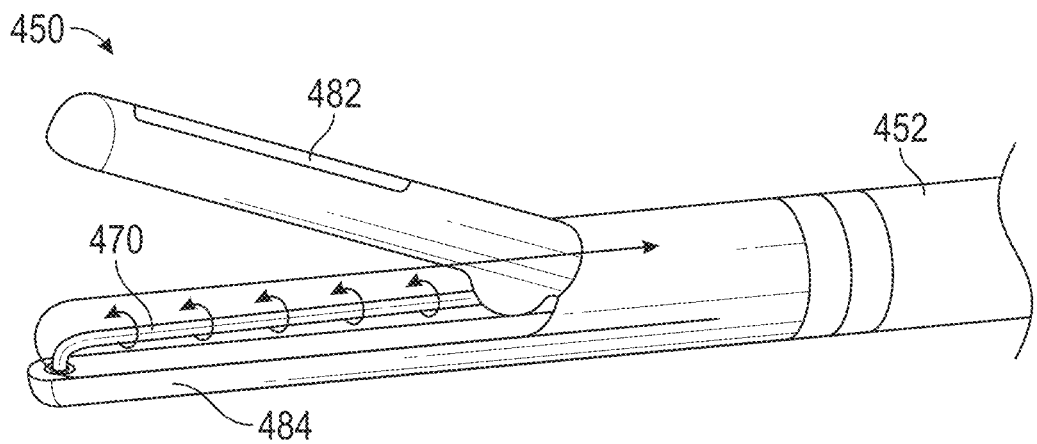
FIG. 29 illustrates the instrument of FIG. 28 while undergoing a magnetic induction.

FIG. 29 illustrates the instrument of FIG. 28 while undergoing a magnetic induction. Magnetic induction allows heat to be generated at the sites of the ferromagnetic coating.

Figure 30:
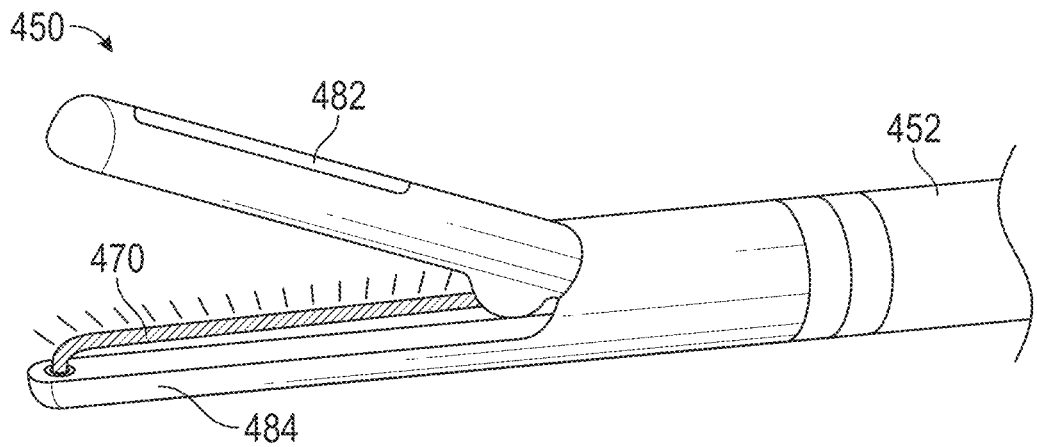
FIG. 30 illustrates the instrument of FIG. 28 while generating heat via magnetic induction.

FIG. 30 illustrates the instrument of FIG. 28 while generating heat via magnetic induction. In some embodiments, the heat can be dissipated along the length of the conductive line 470. In some embodiments, heat can be generated along an entire or substantially entire length of the conductive line 470. In other embodiments, heat can be generated interstitially or intermittently along the length of the conductive line 470.

Figure 31:
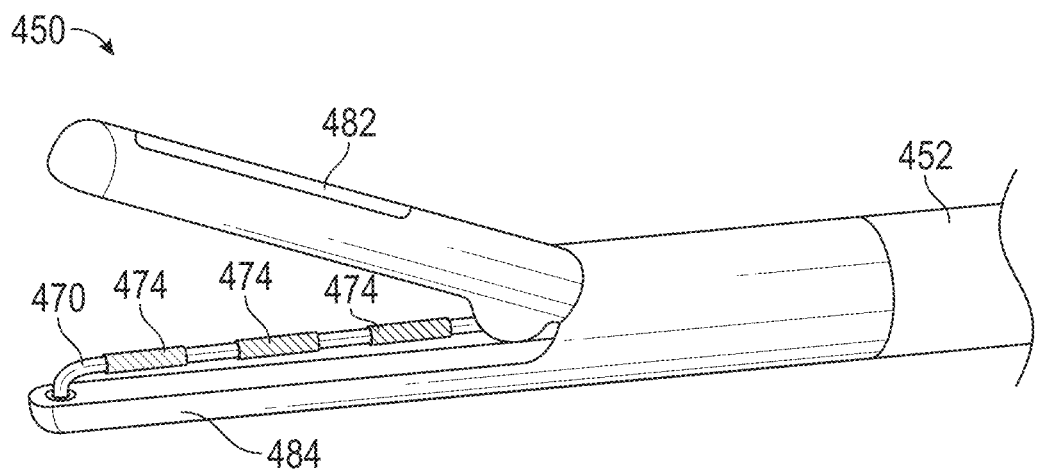
FIG. 31 illustrates a close up view of the instrument of FIG. 28.

FIG. 31 illustrates a close up view of the instrument of FIG. 28. From this view, one can see the upper jaw 482, the lower jaw 484 and the conductive line 470 that extends along a mid-longitudinal axis of the lower jaw 484. The conductive line 470 is coated interstitially or intermittently with a ferromagnetic coating 474, thereby providing sites of different heat along one or more of the jaws. In other embodiments, the ferromagnetic coating 474 is applied continuously along a length of the conductive line 470. In some embodiments, the ferromagnetic coating 474 can be applied directly onto a surface of the conductive line 470. In other embodiments, the ferromagnetic coating 474 can be applied on top of a non-conductive coating 476, which is itself directly applied onto the conductive line 470 (as shown in FIG. 32).

Figure 32:
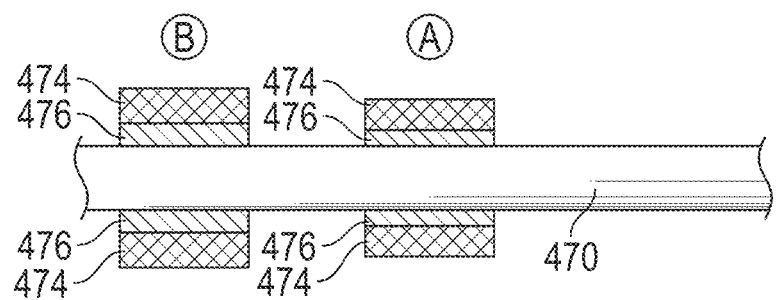
FIG. 32 illustrates a close up view of the conductive line of the instrument of FIG. 28.

FIG. 32 illustrates a close up view of the conductive line of the instrument of FIG. 28. In this embodiment, a ferromagnetic coating 474 is formed interstitially along a length of the conductive line 470. In some embodiments, the thickness of the ferromagnetic coating 474 can be the same or substantially the same along the length of the conductive line. In other embodiments, the thickness of the ferromagnetic coating 474 can vary along the length of the conductive line 470, thereby providing sites of different heat along the upper and lower jaws 482, 484. In the illustrated embodiment, optional non-conductive/insulative coating layers 476 can be deposited between the ferromagnetic coating 474 and conductive line 470. These non-conductive coating layers 476 advantageously aid in rapid cool-down of the multi-functional vessel sealer by providing a point of limited heat transfer. In some embodiments, the thickness of non-conductive coating layers 476 can be the same or substantially the same along the length of the conductive line 470. In other embodiments, the thickness of the non-conductive coating 476 can vary along the length of the conductive line 470.

In the illustrated embodiment, the thickness of the non-conductive coating 476 varies at the two different locations "A" and "B" along the length of the conductive line 470. The thickness of the non-conductive coating 476 is thicker at site "B" than at site "A". The varied thicknesses helps to vary the heat transfer and cooling that can occur at different sites along the length of the conductive line 470.

In some embodiments, rather than coating a conductive line with ferromagnetic material, ferromagnetic beads can be deposited on the surface. In some embodiments, ferromagnetic beads can be deposited via a sputtering or ion implantation process. Such ferromagnetic beads can have the same heat generating effects as a ferromagnetic coating, thereby enabling a multi-functional instrument to serve as both a vessel sealer and cutter via electrical energy, without relying on a physical cutting blade.

Figure 35:
FIG. 35 illustrates a third embodiment of a ferromagnetic bead.
Figure 34:
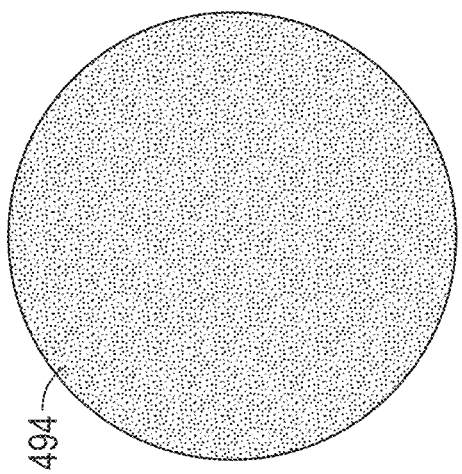
FIG. 34 illustrates a second embodiment of a ferromagnetic bead.
Figure 33:
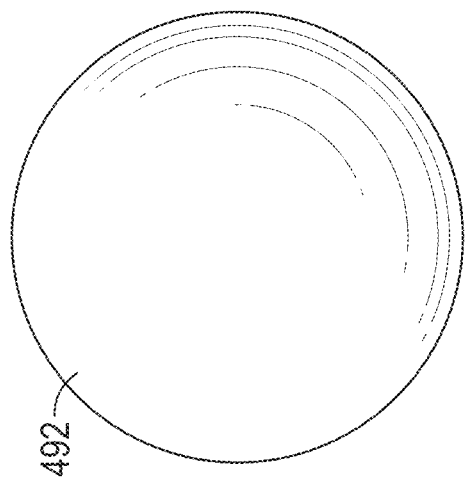
FIG. 33 illustrates one embodiment of a ferromagnetic bead.

FIGS. 33-35 illustrate different embodiments of ferromagnetic beads that can be deposited along a length of a conductive line. Like the ferromagnetic coating, the ferromagnetic beads can be deposited in interstitial clumps, or substantially together along a single length of the conductive line. In some embodiments, the ferromagnetic beads can include any of the following: (i) a solid bead 492 with relatively low surface area (shown in FIG. 33); (ii) a porous bead 494 with relatively larger surface area (shown in FIG. 34); and (iii) a hyperporous bead 496 comprised of a polymer network with even larger surface area (shown in FIG. 35).

As noted above, it can be beneficial to regulate the temperature of the end effector of the multi-functional instrument so as to enable the instrument to perform different functions, such as sealing and cutting. The temperature can be regulated either manually or via a processor that keeps the temperature within a specific range based on a user's desired function.

Figure 36:
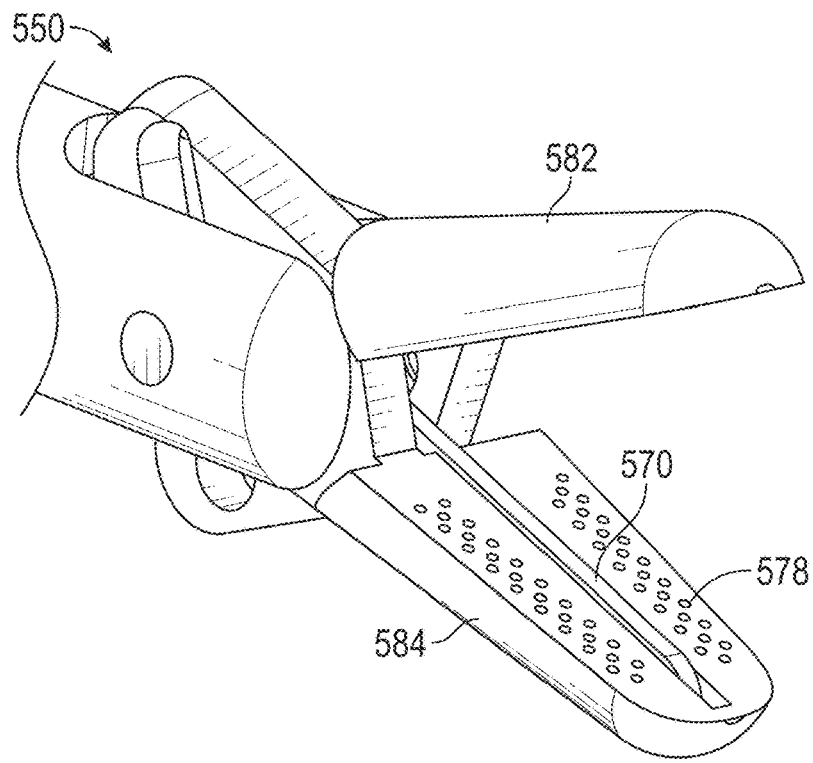
FIG. 36 illustrates a medical instrument having one or more cooling nozzles for regulating temperature of the end effector.

FIG. 36 illustrates a medical instrument 550 having one or more cooling nozzles 578 for regulating temperature of the end effector. The instrument 550 comprises an end effector coupled to a multi-DOF wrist (not shown) that includes an upper jaw 582 and a lower jaw 584. As shown in FIG. 36, within one or both of the jaws 582, 584 is a heating element 570. Like the conductive lines and coils described above, in some embodiments, the heating element 570 can be coated in a ferromagnetic material so as to generate heat via magnetic induction.

To regulate the temperature of the end effector, the instrument 550 further comprises one or more cooling nozzles 578. The cooling nozzles 578 comprise holes or openings for releasing a cooling fluid (e.g., water or saline) to help regulate the temperature of the instrument relative to tissue. This can be beneficial, for example, if a user wants to rapidly switch the heating element 570 from performing one function (e.g., cutting) to another (e.g., sealing), as it may be helpful to have rapid cooling and quenching. As shown in FIG. 36, the holes of the cooling nozzles 578 can be distributed along or adjacent the heating element 570 to provide efficient regulation of temperature based on the desired function of the multi-functional instrument. As an alternative, in some embodiments, cooling fluid can be dispensed through the shaft of the instrument 550, thereby reducing the reliance on a fluid path through the jaws 582, 584.

One skilled in the art will appreciate that any of the embodiments described thus far (and described below) can be attached to a multi-DOF wrist, as shown for example in FIGS. 23-26. In embodiments that utilize a conductive line, coil or heating element, any of these can be formed of a conductive metal or metal alloy. For example, in some embodiments, a conductive line or coil is formed of any of the following materials, either individually or in combination, including copper, aluminum, steel, tungsten, titanium or platinum, or any other type of conductive material.

Furthermore, in embodiments that utilize a ferromagnetic coating or bead, these can be formed of any type of ferromagnetic material, either individually or combination, including ferrous, ferrite and ferrous oxide materials such as NiFe alloy, Fe, Co, FeOFe2O3, NiOFe2O3, Ni, MnSb, Gd, Dy, MnOFe2O3, CuOFe2O3, or any other type of ferrous material. In some embodiments, the ferromagnetic coating or bead can have a thickness of between 0.1 mm and 550 mm, or between 0.05 mm and 550 mm, or between 1 mm and 60 mm.

In tissue sealer and cutter embodiments described above, a conductive line or coil can be resistively heated to advantageously perform multiple functions, such as sealing, hemostasis or cutting. In some embodiments, the conductive line or coil can be placed along a midline of a tissue sealer jaw, while in other embodiments, the conductive line or coil can be placed offset from a midline of the tissue sealer or jaw. As the conductive line or coil generates heat (e.g., via magnetic induction), it may be unnecessary in some circumstances to provide a physical, sharp cutting element (e.g., a blade or scythe). However, one skilled in the art will appreciate that in some instances, it may be desirable to have a sharp blade for cutting in lieu of or in addition to energy delivering modalities.

ii. Rotating Electrodes

In an alternative embodiment, rather than providing a tissue sealer and cutter that generates heat via magnetic induction (e.g., via ferromagnetically coated conductive lines), a tissue sealer and cutter can be provided that utilizes one or more fixed electrodes in combination with one or more rotating electrodes to perform multiple functions, such as sealing and cutting.

Figure 37A:
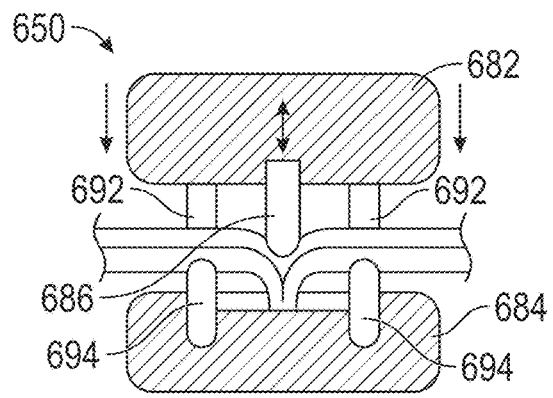
FIGS. 37A and 37B illustrate a medical instrument having rotating electrodes for sealing and cutting tissue.
Figure 37B:
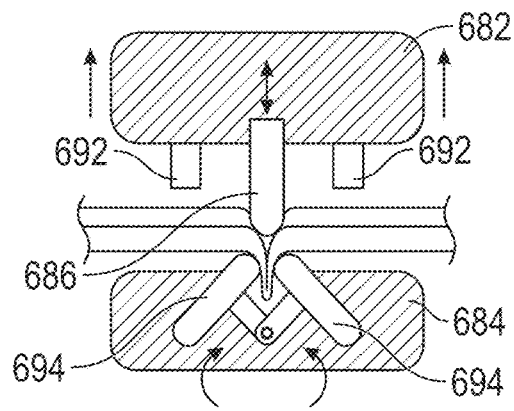

FIGS. 37A and 37B illustrate a multi-functional medical instrument 650 having rotating electrodes 694 for sealing and cutting tissue. The instrument 650 comprises an upper jaw 682 and a lower jaw 684. The upper jaw 682 includes a movable mandrel 686 that can force tissue into a notch formed on the opposing lower jaw 684. This formation of the tissue can be referred to as plication, with the purpose being to "fold" the tissue, and thereby allow dividing elements (e.g., rotating electrodes) to sever the tissue into two.

The instrument 650 can include both fixed electrodes 692 and rotating electrodes 694 to assist in sealing and cutting. The instrument 650 comprises a tissue sealer including rotating electrodes 694 that initially seal clamped tissue, and then rotate into position to divide the tissue.

FIG. 37A shows the instrument 650 and its electrodes 692, 694 in a sealing configuration. In this configuration, the upper jaw 682 is positioned relative to the lower jaw 684 such that the movable mandrel 686 of the upper jaw 682 forces tissue into a notch of the lower jaw 684. Such plication by the movable mandrel 686 can also be achieved by other mechanical manipulation, suction, positive air pressure, etc. In the sealing configuration, the axes of the fixed electrodes 692, which are coupled to the upper jaw 682, are in substantial alignment with the axes of the rotating electrodes 694, which are coupled to the lower jaw 684. In this configuration, as the electrodes 692, 694 are heated, tissue is sealed between the jaws 682, 684.

FIG. 37B shows the instrument 650 and its electrodes 692, 694 in a cutting or dividing configuration. In this configuration, the rotating electrodes 694 have been rotated such that their axes are not in alignment with the fixed electrodes 692. Rotation of the electrodes 694 provides a cutting mechanism that cuts the tissue. In this configuration, the upper jaw 682 has been displaced further from the lower jaw 684. The electrodes 692, 694 can be heated electrically, ultrasonically, or even cryo chilled to create a seal and/or division of tissue.

iii. Heated Fluids

While the embodiments above describe a tissue sealer and cutter that utilize different types of energy modalities, such as electrical heating and magnetic induction to perform sealing and cutting, in some embodiments, fluids can be used to perform sealing and/or cutting.

Figure 38:
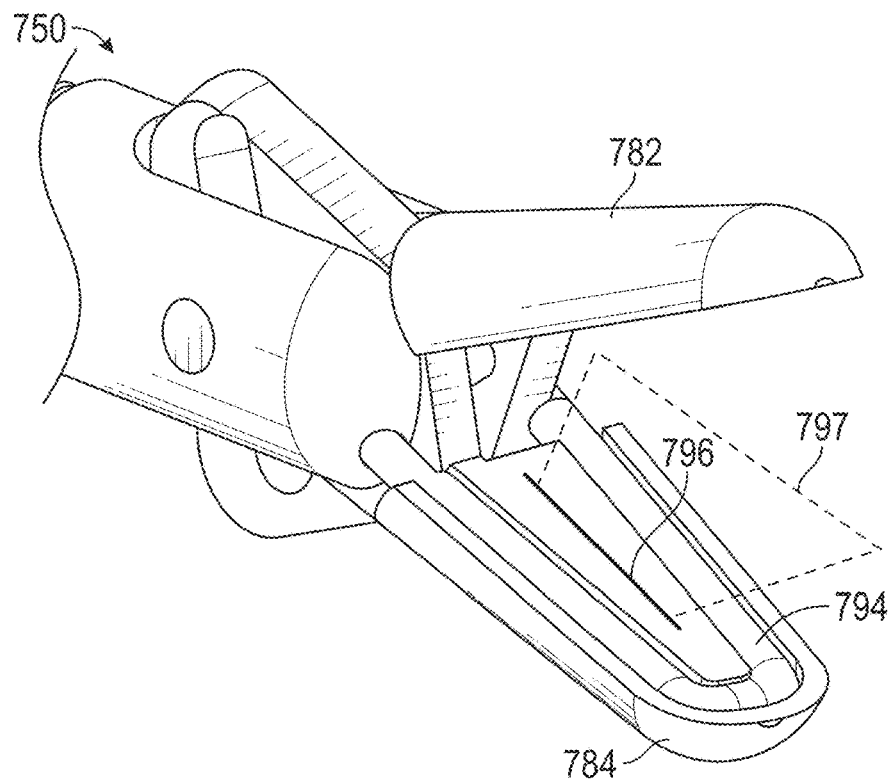
FIG. 38 illustrates a medical instrument having a fluidic cutting nozzle.

FIG. 38 illustrates a medical instrument 750 having a fluidic cutting nozzle 796. The medical instrument 750 can include a multi-DOF wrist (not shown) and can be robotically controlled. The instrument 750 comprises an end effector including an upper jaw 782 and a lower jaw 784, wherein one or both of the jaws 782, 784 can be lined with a heated fluid conduit 794. The heated fluid conduit 794 can advantageously be used to circulate a heated fluid to perform a desired function, such as sealing. In addition, the one or both of the jaws 782, 784 can include a cutting nozzle 796 whereby a stream or jet of heated fluid 797 can be delivered to perform a different function, such as cutting. Advantageously, like other embodiments, this tissue sealer and cutter embodiment does not rely on a sharp cutting blade.

B. Bladed Instruments with Thermal Capabilities.

In many of the tissue sealer and cutter embodiments described above, different energy modalities are used to replace a sharp cutting blade. In some embodiments, however, it may be advantageously to include a sharp cutting blade. Accordingly, the embodiments described herein include one or more optional cutting elements (e.g., blades), in addition to being able to deliver energy for sealing, hemostasis or cauterization.

Figure 39:
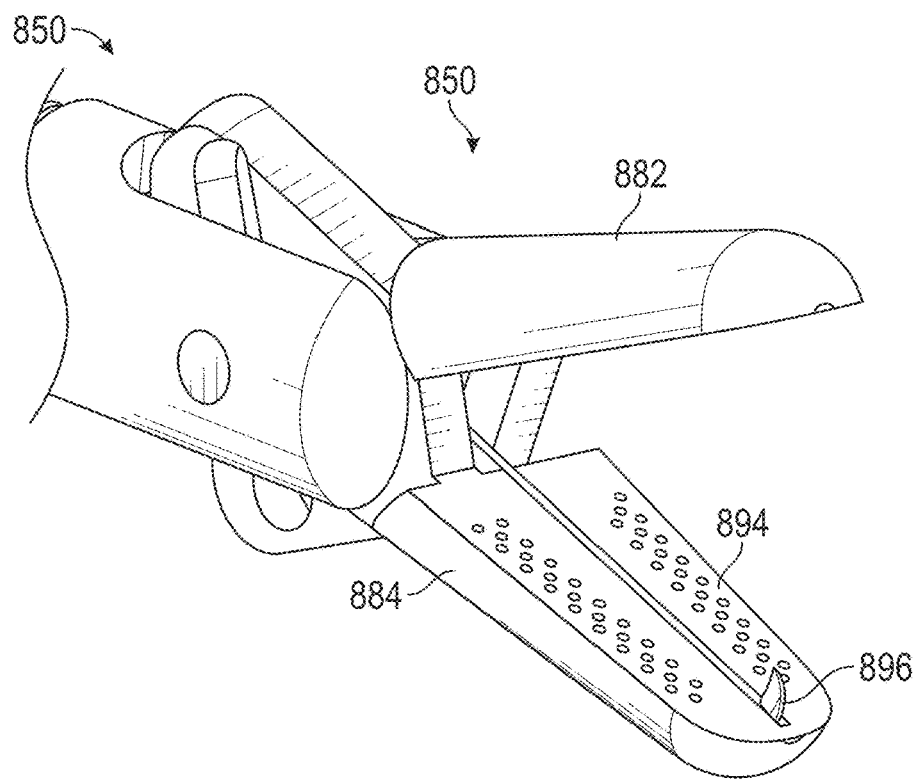
FIG. 39 illustrates a medical instrument having steam nozzles.

FIG. 39 illustrates a medical instrument 850 having steam nozzles 894 with an optional cutting blade 896. The medical instrument 850 comprises an upper jaw 882 and a lower jaw 884, wherein one or both of the jaws 882, 884 comprises one or more steam nozzles 894 with holes or openings for deploying steam. In some embodiments, the steam can be used to perform sealing, hemostasis or cauterization. Temperature of the steam can be tightly controlled via pressure and as needed, a volume of cooling fluid can also be flushed through the one or more steam nozzles 894 to cool the area.

For cutting or dividing the tissue, a pull blade 896 can be actuated via a cable after the jaws 882, 884 have been closed and sealing has been achieved. As shown in FIG. 39, the pull blade 896 is coupled to an elongated shaft that extends through a slot of the lower jaw 884. In some embodiments, the pull blade 896 and its elongated shaft can be replaced via a conductive line (e.g., one that may be coated with a ferromagnetic material), such that resistive heating can be used to perform a cutting or dividing function. In some embodiments, a processor (such as described with respect to the flow chart in FIG. 22), can regulate the temperature of such a conductive line and the steam nozzles to enable the end effector to perform multiple functions at different temperatures. In some embodiments, a conductive line can be used for cutting while the holes 894 can be used to deploy steam for sealing. In other embodiments, a conductive line can be used for both cutting and sealing, while the holes 894 can be used to deploy simply a cooling fluid for temperature regulation.

Figure 40:
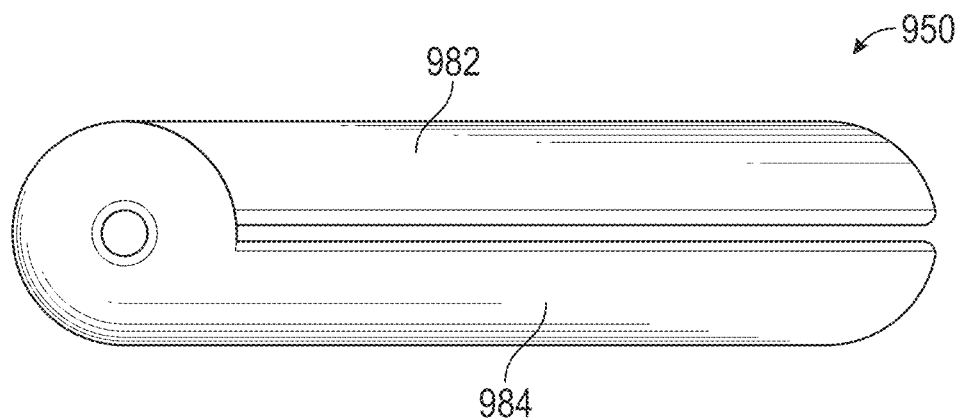
FIG. 40 illustrates a medical instrument having a mechanical cutting element.

FIG. 40 illustrates an alternative embodiment of medical instrument 950 having a mechanical cutting element. In this embodiment, the medical instrument comprises a tissue sealer and cutter that includes an upper jaw 982 and a lower jaw 984, wherein the lower jaw 984 houses a cutting element 996 in the form of a wire or ribbon blade that projects outwardly towards the upper jaw 982. The cutting element 996 can be housed in a slot formed in the lower jaw 984. In some embodiments, the cutting element 996 can be deployed and can have various types of motion, including a "snare"-like motion, a spring-like motion, a lateral driven motion (e.g., created through/by a balloon), or push motion (e.g., via a push plate). In some embodiments, the cutting element 996 can be heated or cooled using any of the mechanisms described above. For example, in some embodiments, the cutting element 996 can be coated by a ferromagnetic material to enable magnetic induction heating. In other embodiments, the cutting element 996 can be coupled to a conductive line that is in part coated by a ferromagnetic material.

Figures 41, 42:
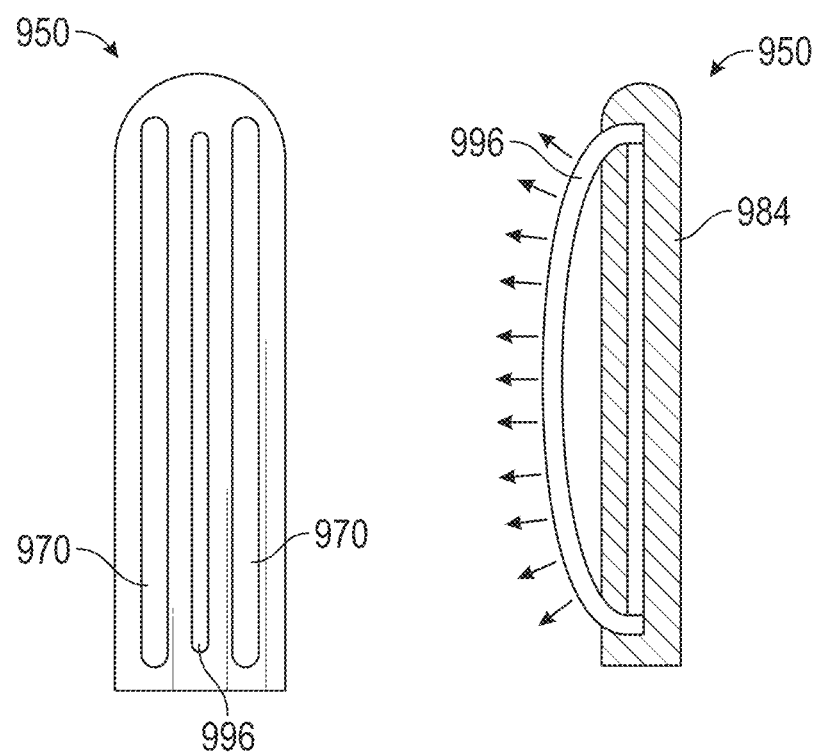
FIG. 41 illustrates a top cross-sectional view of the medical instrument of FIG. 40.
FIG. 42 illustrates a side view of the medical instrument of FIG. 40.

FIG. 41 illustrates a top cross-sectional view of the medical instrument of FIG. 40. As shown in FIG. 41, the cutting element 996 can be positioned between sealing elements 970. The sealing elements 970 can be a conductive member that is heated via various modalities, including electrical heating, induction heating, or RF heating.

FIG. 42 illustrates a side view of the medical instrument of FIG. 40. From this view, one can see the cutting element 996 (e.g., a blade) that can be heated or cooled (e.g., via induction heating). As shown in the figure, the cutting element 996 is in the process of being heated. Advantageously, the cutting element 996 can be heated to a different temperature from the sealing elements 970 with ease, such that the end effector is capable of multiple functions.

Figure 43:
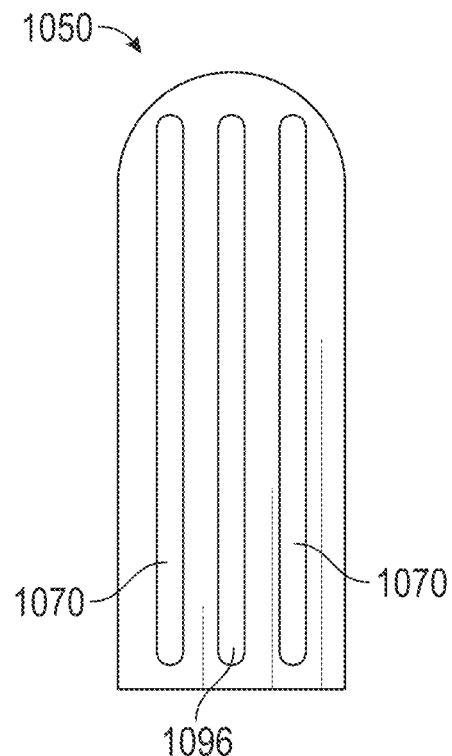
FIG. 43 illustrates a medical instrument having a mechanical cutting element and rotating electrodes.

FIG. 43 illustrates a medical instrument 1050 having a mechanical cutting element 1096 and rotating electrodes 1070. The medical instrument 1050 comprises a tissue sealer and cutter comprising a cutting element 1096 (e.g., a cutting wire or blade) adjacent one or more electrodes 1070 that are capable of rotation. By rotating the electrodes 1070, this advantageously allows the jaws 1082, 1084 to be driven into tissue with different torques and pressures. In some embodiments, torque value can correlate to a given clamping pressure exerted/imparted onto tissue. In some embodiments, the cutting element 1096 can be heated or cooled using any of the mechanisms described above. For example, in some embodiments, the cutting element 1096 can be coated by a ferromagnetic material. In other embodiments, the cutting element 1096 can be coupled to a conductive line that is in part coated by a ferromagnetic material.

Figure 44:
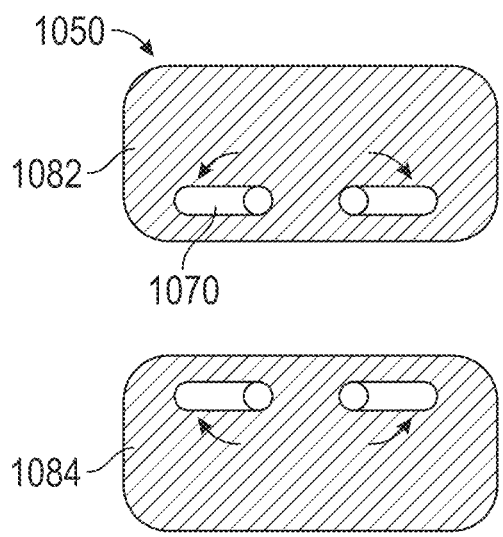
FIG. 44 illustrates a front view of the medical instrument of FIG. 43 in a first configuration.

FIG. 44 illustrates a front view of the medical instrument 1050 of FIG. 43 in a first configuration. In this configuration, the rotatable electrodes 1070 are in a "home" or "inactive" position, whereby the rotatable electrodes 1070 do not apply pressure and contact tissue between the jaws 1082, 1084.

Figure 45:
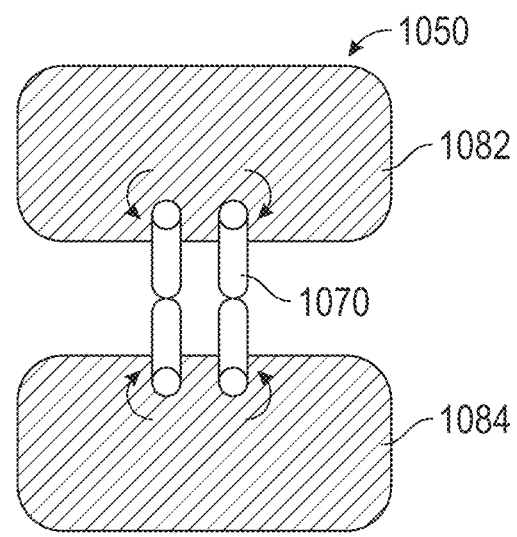
FIG. 45 illustrates a front view of the medical instrument of FIG. 43 in a second configuration.

FIG. 45 illustrates a front view of the medical instrument 1050 of FIG. 43 in a second configuration. In this configuration, the rotatable electrodes 1070 are in an "active" position, whereby the rotatable electrodes 1070 apply pressure and contact tissue to perform a sealing function between the jaws 1082, 1084.

Figure 46:
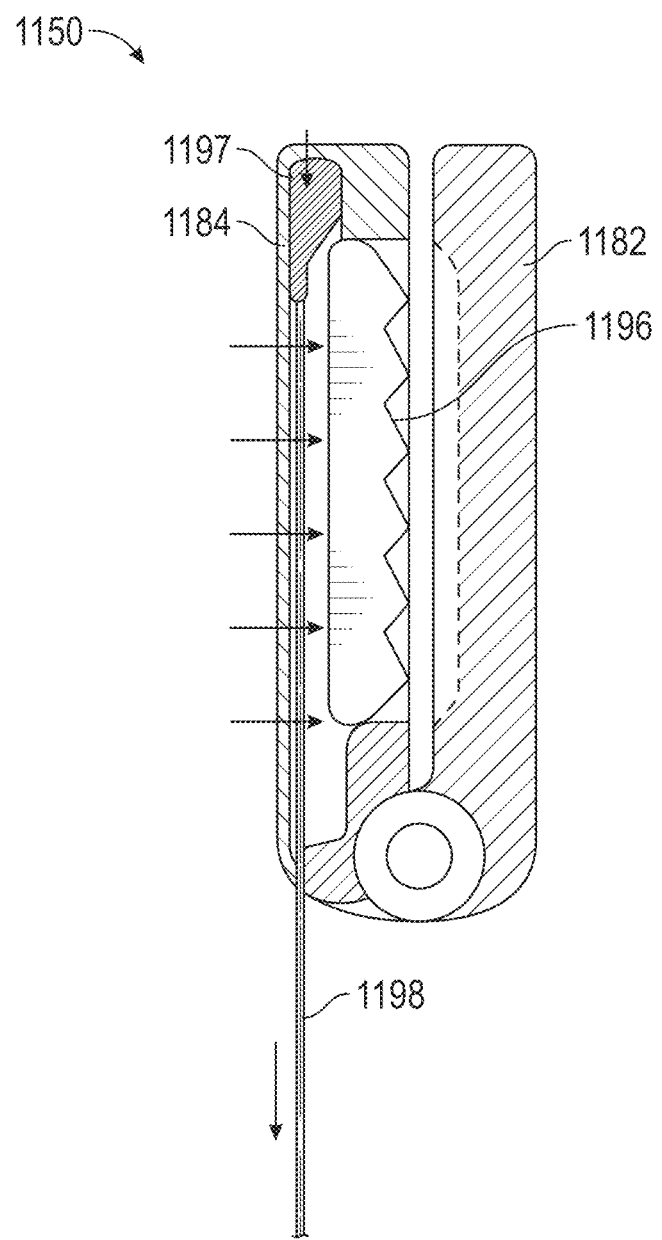
FIG. 46 illustrates a medical instrument having a mechanical cutting element deployable by a sliding wedge.

FIG. 46 illustrates a medical instrument 1150 having a mechanical cutting element 1196 deployable by a sliding wedge 1197. The medical instrument 1150 comprises a tissue sealer and cutter including an upper jaw 1182 and a lower jaw 1184, wherein the lower jaw 1184 houses a cutting element 1196 (e.g., a cutting blade). In the present embodiment, the cutting element 1196 has a unique deployment mechanism. As shown in FIG. 46, the cutting element 1196 is capable of being deployed via a sliding wedge 1197 that is coupled to a pull cable 1198. As the sliding wedge 1197 is pulled along the pull cable 1198, this deploys the cutting blade in a non-translational fashion. In some embodiments, the cutting element 1196 can be connected to a heating or cooling elements that allows for temperature adjustment of the cutting element 1196.

Figure 47:
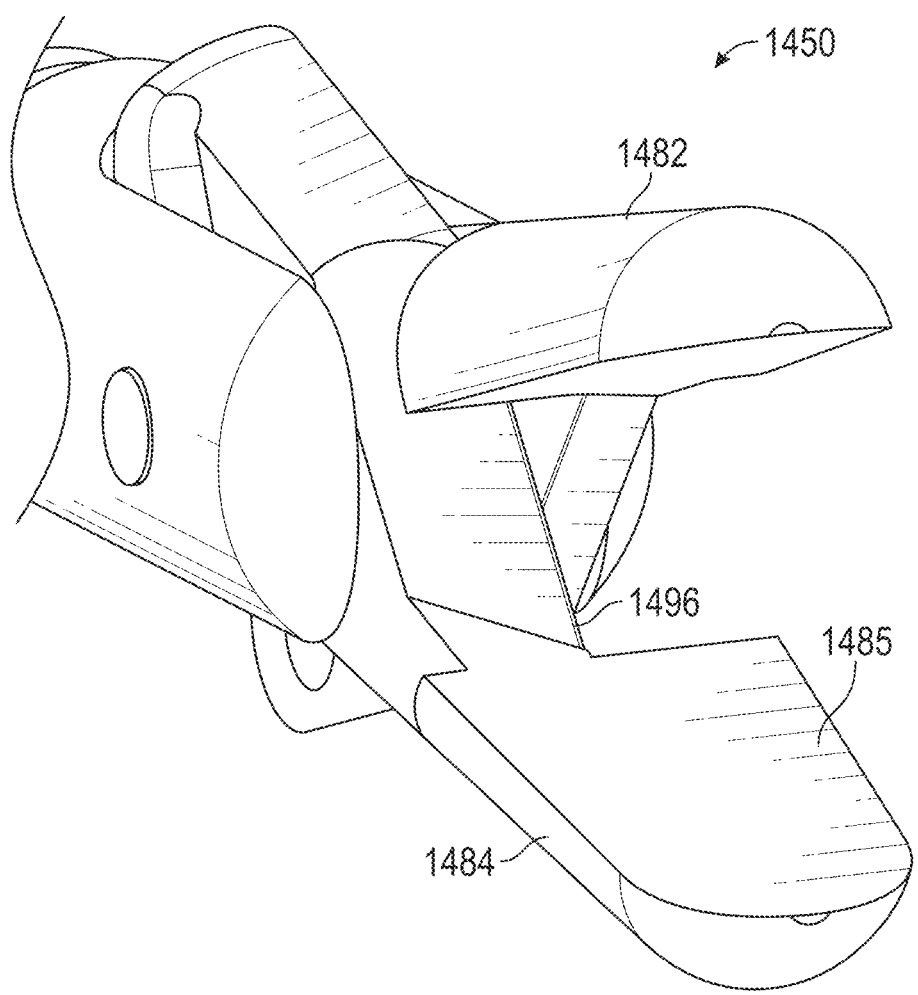
FIG. 47 illustrates a medical instrument having an inner shear interface.

FIG. 47 illustrates a medical instrument 1450 having an inner shear interface 1496. In this embodiment, the medical instrument 1450 comprises a tissue sealer and cutter having an upper jaw 1482 and a lower jaw 1484 with shears or scissors 1496 that are integrated or incorporated into a backside of the jaws. After vessel sealing is achieved on the face 1485 of the jaws 1482, 1484 (e.g., via electrical, induction and/or RF heating), the surgical shears 1496 can be actuated to divide desired tissue. Advantageously, the jaws 1482, 1484 can be actuated robotically (e.g., via actuation cables) to increase cutting efficiency and efficacy.

Figure 48:
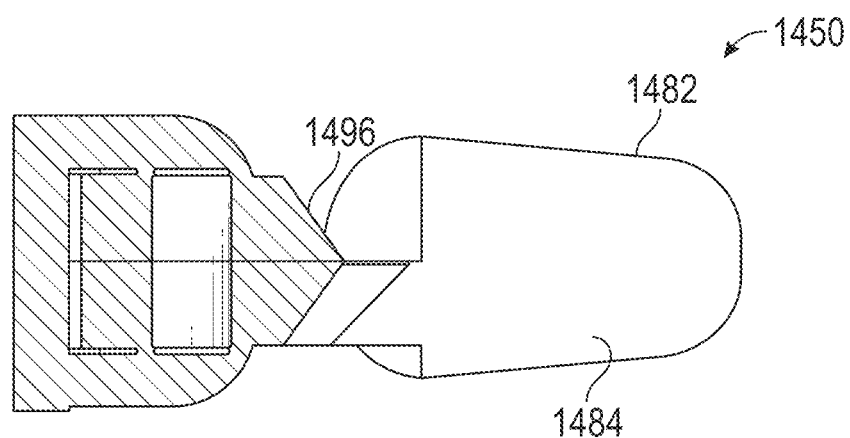
FIG. 48 illustrates a side cross-sectional view of the medical instrument of FIG. 47.

FIG. 48 illustrates a side cross-sectional view of the medical instrument of FIG. 47. From this view, one can see the relative position of the surgical shears 1496 to the grasping and sealing jaws 1482, 1484. Advantageously, the surgical shears 1496 are in a removed position from the grasping and sealing jaws 1482, 1484 such that the risk of inadvertent cutting of tissue is reduced.

C. Instruments with Lasers.

In addition to the instruments described above that are capable of using various energy modalities (e.g., electrical, magnetic induction and/or RF) to accomplish different functions, such as tissue sealing and cutting, instruments are also provided that utilize a novel laser feature.

Figure 49:
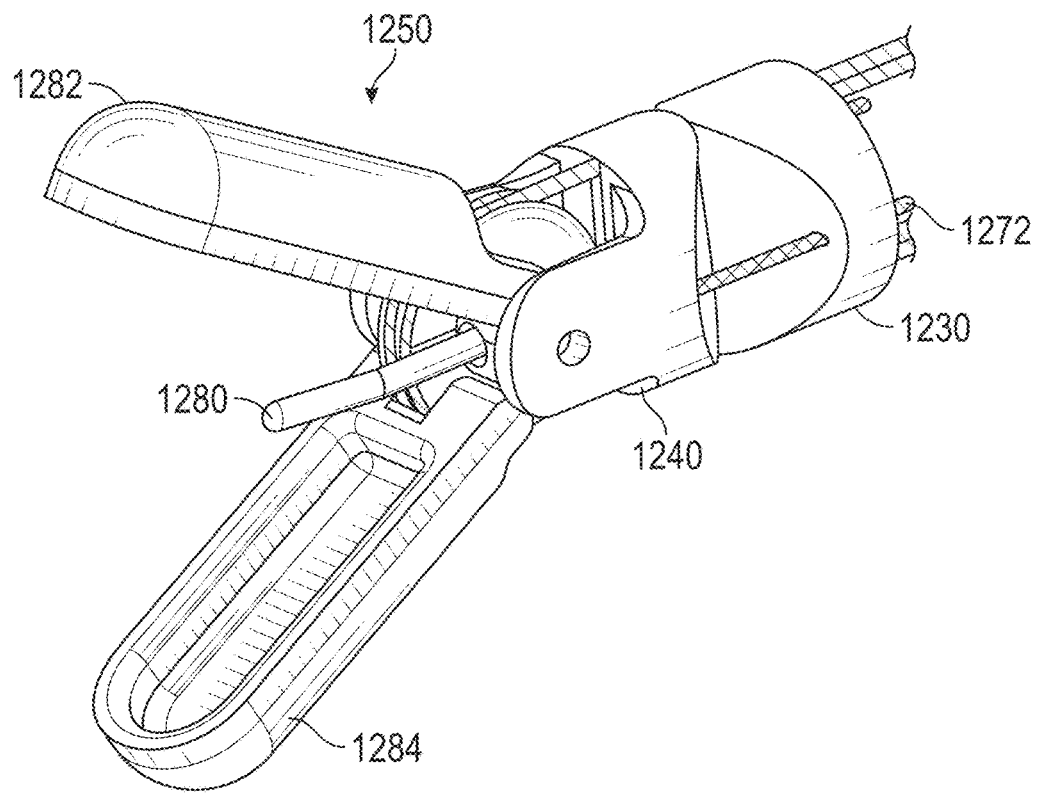
FIG. 49 illustrates a medical instrument having a laser.

FIG. 49 illustrates a medical instrument 1250 having a laser. The medical instrument 1250 comprises a tissue sealer and cutter comprising a multi-DOF wrist including a proximal clevis 1230 and a distal clevis 1240 capable of articulation via one or more drive or articulation cables 1272. The wrist is coupled to an end effector comprising an upper jaw 1282, a lower jaw 1284, and a laser carrier, vessel or fiber 1280. In some embodiments, the upper jaw 1282 and lower jaw 1284 can be used for grasping and sealing of tissue, while the laser 1280 can be used for tissue cutting.

As shown in FIG. 49, the upper jaw 1282 and lower jaw 1284 have closed outer surfaces. The jaws 1282, 1284 each have a rim feature, so that tissue can be grabbed using the sides of the jaws. This is advantageous, as it allows the central portion of the vessel sealer to remain untouched and available for use (e.g., such as by the laser fiber 1280). In some embodiments, the rim of the jaws 1282, 1284 can be heated using any of the heat modalities described above, thereby performing sealing, hemostasis or cauterization. On the other hand, the laser 1280 can be used to perform a different function, such as cutting. The laser 1280 can be minutely maneuverable to move either forward and back, or up and down, or in combined directions, to fire into tissue. Using the instrument 1250 of FIG. 49, a clinician or surgeon can both properly grasp tissue and cut tissue (e.g., via laser cutting) safely and efficiently.

Figure 50:
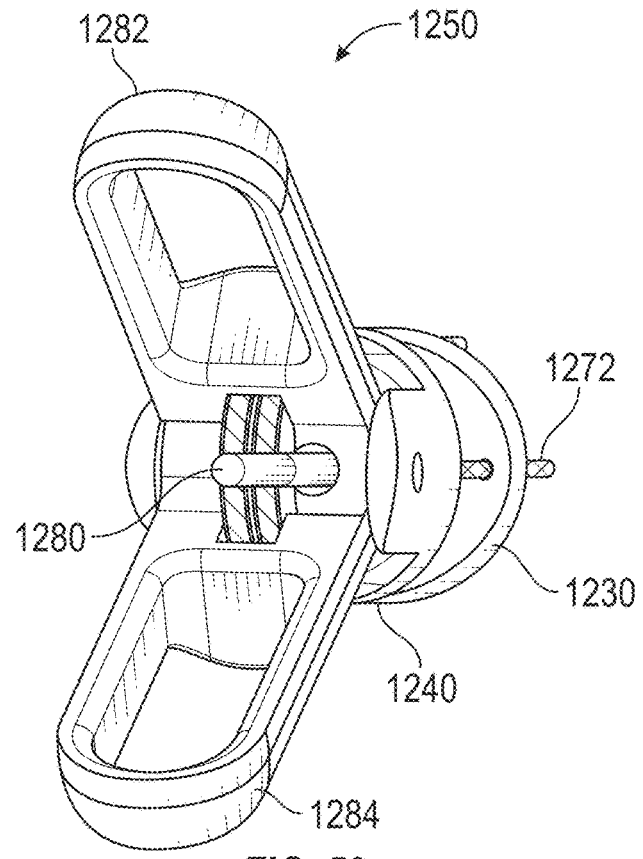
FIG. 50 illustrates an alternative embodiment of a laser with open jaws.

FIG. 50 illustrates an alternative embodiment of a medical instrument 1250 having a laser. The medical instrument 1250 serves as a tissue sealer and cutter, and includes similar features to the embodiment in FIG. 49, including a multi-DOF wrist, one or more articulation cables 1272, and an end effector having upper and lower jaws 1282, 1284. However, in the present embodiment, the upper and lower jaws 1282, 1284 are now provided with windows. By providing such windows, a clinician or surgeon can advantageously view the area that the laser 1280 is firing at.

Figure 51:
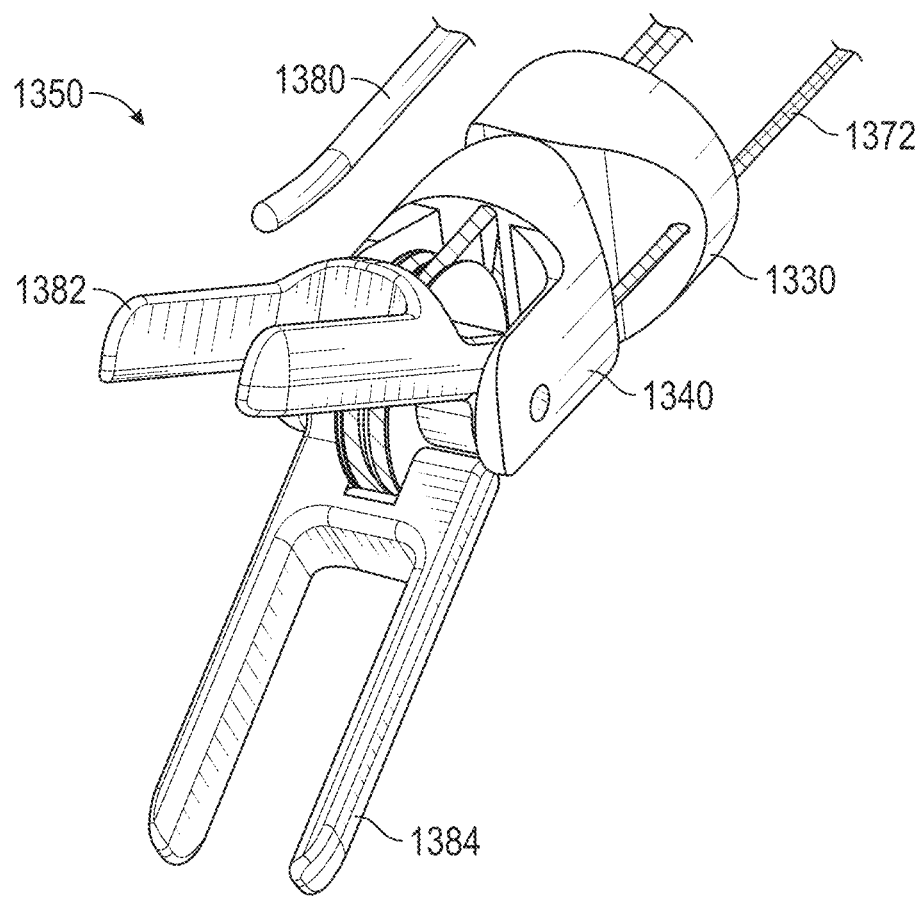
FIG. 51 illustrates an alternative embodiment of a medical instrument having a laser and fork-like jaws.

FIG. 51 illustrates an alternative embodiment of a medical instrument 1350 having a laser and fork-like jaws 1382, 1384. The medical instrument 1350 serves as a tissue sealer and cutter, and includes similar features to the embodiment in FIG. 49, including a multi-DOF wrist, one or more articulation cables 1372, and an end effector having upper and lower jaws 1382, 1384. However, in the present embodiment, the upper and lower jaws 1382, 1384 are in the form of protruding forks. By using protruding forks, this provides maximum visibility from three sides once tissue is grabbed.

D. Cooling Mechanisms

In the above described embodiments, a number of multi-functional instruments are described using different energy modalities for different functions, including sealing, hemostasis, cauterization and/or cutting. In this section, unique cooling mechanisms will be described that can be incorporated into any of the instruments described above. These cooling mechanisms can be used to regulate temperature so that the instrument and its end effector can perform different functions, such as cutting and sealing. In addition, these cooling mechanisms advantageously provide rapid cooling to the overall instrument and its architecture, thereby reducing the risk of inadvertent burns on tissue adjacent to the instrument.

Figure 52:
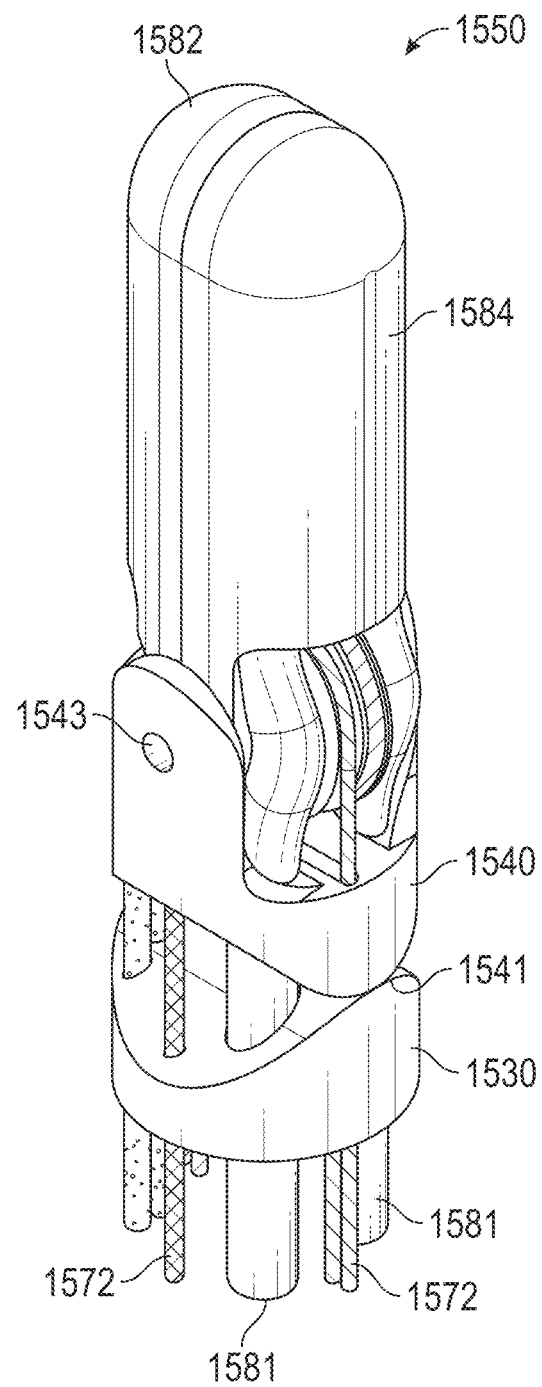
FIG. 52 illustrates a medical instrument including a fluidic cooling system.

FIG. 52 illustrates a medical instrument 1550 including a fluidic cooling system. The medical instrument 1550 comprises a tissue sealer and cutter that is capable using different energy modalities to seal and cut tissue. The instrument 1550 comprises a multi-DOF wrist including a proximal clevis 1530 and a distal clevis 1540, with the distal clevis 1540 being a frankenclevis having a rolling joint 1541 near its lower portion and a pin joint 1543 along its upper portion. The instrument 1550 includes one or more drive or articulating cables 1572 for articulating the wrist and the end effector. The end effector comprises an upper jaw 1582 and a lower jaw 1584 capable of performing a number of functions on tissue, including sealing, hemostasis, cauterization and cutting. One or more of the jaws 1582, 1584 can be used to deliver any of the energy modalities described above, including electrical, magnetic induction or RF energy.

The medical instrument 1550 further comprises a fluidic cooling system that allows a cooling fluid (e.g., water or saline) to flow throughout the instrument architecture. The instrument 1550 comprises a vessel, lumen, tube or conduit 1581 that extends from the wrist through the end effector (as shown best in FIGS. 54 and 56). Cooling fluid is capable of circulating through the conduit 1581 and into the grips/jaws 1582, 1584, to thereby regulate temperature of the instrument. Advantageously, a processor can be provided that controls the pump rate, overall flow and temperature of the fluid through the conduit 1581.

FIG. 53 illustrates a front perspective view of the medical instrument of FIG. 52 with one of the jaws removed. From this view, one can see the unique wristed architecture including the proximal clevis 1530, distal clevis 1540 and the pulley 1544 positioned within the distal clevis 1540.

FIG. 54 illustrates a front perspective view of the medical instrument of FIG. 52 with one of the jaws removed and the other jaw exposed. From this view, one can see the path of the fluid conduit 1581 as it extends through the wrist and into the grip/jaw 1584 of the end effector.

FIG. 55 illustrates a side view of the medical instrument of FIG. 52 with one of the jaws removed. From this view, one can see the unique architecture of wrist as it transitions to the end effector.

FIG. 56 illustrates a side view of the medical instrument of FIG. 52 with one of the jaws removed and the other jaw exposed. From this view, one can see the path of the fluid conduit 1581 as it extends through the grip/jaw 1584. Advantageously, as fluid moves through the conduit 1581, the fluid absorbs heat in the jaws 1582, 1584 and removes it from the working site. In some embodiments, the fluid moves due to a pressure differential created outside of the instrument.

Figure 57:
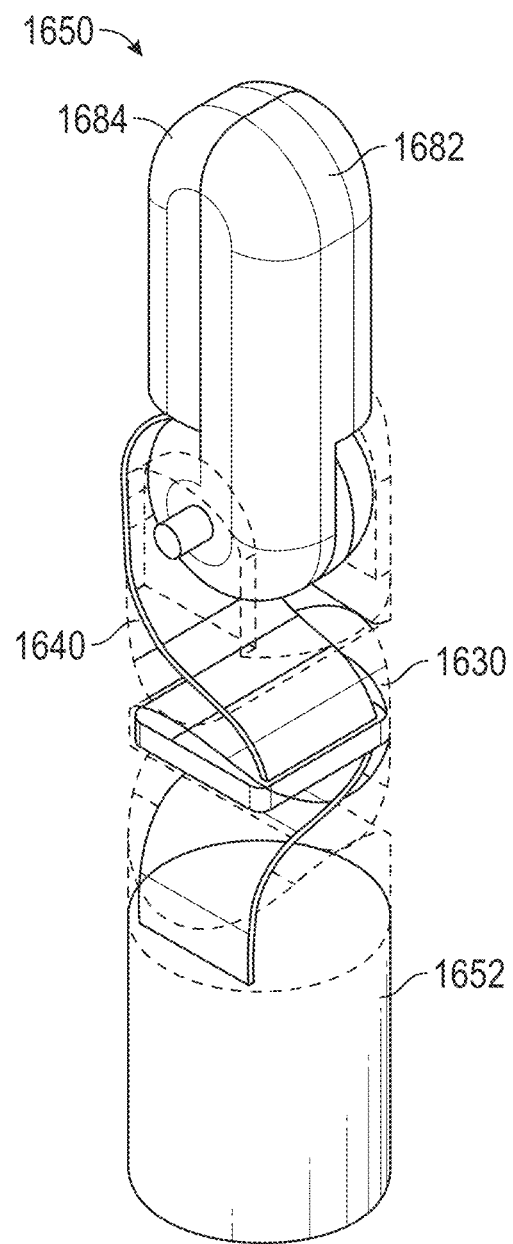
FIG. 57 illustrates a medical instrument including one or more flexures for thermal transfer and cooling.

FIG. 57 illustrates a medical instrument 1650 including one or more flexures for thermal transfer and cooling. Rather than using a fluid conduit as in FIG. 57, this embodiment utilizes flexure conductors 1640 to remove heat from the jaws 1682, 1684 and back to the instrument shaft 1652. The medical instrument 1650 comprises a tissue sealer and cutter comprising an elongated shaft 1652, a multi-DOF wrist in the form of a snake wrist 1630 connected to the shaft 1652, and an end effector in the form of an upper jaw 1682 and a lower jaw 1684 connected to the snake wrist 1630. The upper and lower jaws 1682, 1684 are capable of using any of the energy modalities described above, including electrical, induction, laser, or RF energy to perform any number of functions, including sealing, hemostasis, cauterization or cutting.

The instrument 1650 includes a unique cooling system in the form of flexure conductors 1640 that extend along the portions of the wrist and/or jaws. Representative locations of the flexure conductors 1640 are shown best in FIGS. 58 and 60. The instrument 1650 uses the flexure conductors 1640 as a means for cooling by providing a thermal transfer/heat sink from a distal portion of the instrument back to a proximal portion of the instrument. For example, the flexure conductors 1640 can provide a cooling heat transfer from the heated end effector, to the wrist, and back to the shaft (which contains a large thermal mass), in accordance with some embodiments.

FIG. 58 illustrates a side view of the medical instrument 1650 of FIG. 57, while FIG. 59 illustrates a side view of the medical instrument of FIG. 57 in an articulated configuration. From this view, one can see the elongated shaft 1652, proximal and distal links 1632, 1634 of the snake wrist 1630, and the lower jaw 1684. In addition, one can see a flexure conductor 1640 that extends through from the rolling joint between the distal link 1634 to the proximal link 1632 of the snake wrist 1630. The flexure conductor 1640 terminates at the distal portion of the elongated shaft 1652. Advantageously, the flexure conductor 1640 includes a shape that allows it to bend with the rolling joint while maintaining length conservation.

FIGS. 60 and 61 illustrate an alternative embodiment of a medical instrument in closed and open positions including one or more flexure conductors. While the present embodiment is similar to the embodiment in FIGS. 58 and 59, the flexure conductor 1640 is along a more extended path. In the present embodiment, the flexure conductor 1640 extends from the grips/jaws 1682, 1684, and through the snake wrist including its rolling joint. In some embodiments, the flexure conductor 1640 can also extend and terminate at the elongated shaft 1652 (as in FIGS. 58 and 59). In the present embodiment, heat is transferred from the jaws to the snake wrist. Advantageously, the flexure is configured to expand outward (as shown in FIG. 61) when the grip is open.

Figure 62:
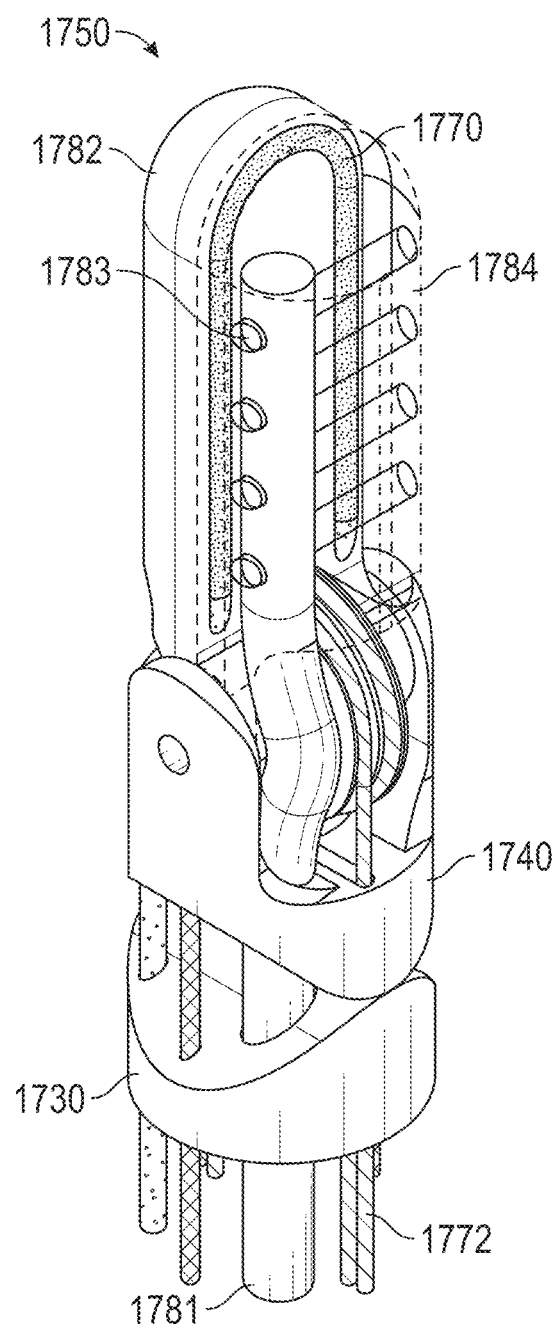
FIG. 62 illustrates a medical instrument with fluid outlets for cooling.

FIG. 62 illustrates a medical instrument 1750 with fluid outlets for cooling. The medical instrument 1750 comprises a tissue sealer and cutter comprising an elongated shaft (not shown), a multi-DOF wrist including a proximal clevis 1730 and a distal clevis 1740, and an end effector including an upper jaw 1782 and a lower jaw 1784. The jaws 1782, 1784 of the instrument 1750 comprises one or more conductive lines 1770 for generating heat (e.g., via magnetic induction) to perform any of the following functions mentioned above, including sealing and cutting. The instrument 1750 further comprises a lumen, tube or conduit 1781 that extends through the wrist and into one or more of the jaws 1782, 1784. At the distal portion of the conduit 1781, outlets 1783 are provided for dripping or spraying water and/or saline for temperature regulation and cooling. Cooling saline can absorb heat when it is in contact with the jaw. The saline then drips off the instrument and into the body.

Any of the cooling mechanisms described in this section can be incorporated with the instrument architectures described above. In addition, these cooling mechanisms can be robotically controlled or otherwise automated.

3. Implementing Systems and Terminology

Implementations disclosed herein provide system, methods, and apparatus for robotically-enabled medical systems. Various implementations described herein include robotically-enabled medical systems with a wrist comprising one or more pulleys shared by cable segments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

Robotic motion, as well as desired instrument parameters (e.g., specific temperature ranges to perform different functions), as described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A multi-functional medical instrument comprising:
a shaft;
a wrist coupled to the shaft, wherein the wrist is movable in at least two degrees of freedom; and
an end effector configured to generate heat to perform sealing or cutting, the end effector comprising:
a non-bladed first jaw comprising a first pad;
a non-bladed second jaw comprising a second pad; and
a conductive line disposed adjacent to the first pad and forming a loop substantially around a perimeter of the first pad and adjacent to the second pad and forming a loop substantially around a perimeter of the second pad, wherein the conductive line is coated with a ferromagnetic coating.

2. The instrument of claim 1, wherein an insulative coating is positioned between the conductive line and the ferromagnetic coating.

3. The instrument of claim 1, wherein the ferromagnetic coating is distributed intermittently along a length of the conductive member.

4. The instrument of claim 3, wherein a thickness of the ferromagnetic coating varies along the length of the conductive member.

5. The instrument of claim 1, wherein the end effector generates heat via fluidics.

6. The instrument of claim 5, wherein the end effector comprises a fluid conduit for circulating heated fluid for sealing and a cutting nozzle for delivering a heated fluid for cutting.

7. The instrument of claim 1, further comprising:
a second conductive line disposed adjacent to the second pad and forming a loop substantially around a perimeter of the second pad, wherein the second conductive line is coated with a ferromagnetic coating.

8. A medical system comprising:
a robotic arm;
an instrument coupled to the robotic arm, the instrument comprising:
a shaft;
a wrist coupled to the shaft; and
an end effector configured to generate heat to perform sealing and cutting functions, the end effector comprising:
a non-bladed first jaw comprising a first pad;
a non-bladed second jaw comprising a second pad; and
a conductive line disposed adjacent to the first pad and forming a loop substantially around a perimeter of the first pad, wherein the conductive line is coated with an intermittent ferromagnetic coating; and
a processor configured to modulate a temperature of the end effector to enable two different functions to be performed.

9. The medical system of claim 8, wherein the processor is configured to modulate a temperature of the conductive line to enable both sealing and cutting functions.

10. The medical system of claim 8, wherein the processor is configured to modulate a temperature of the conductive pad to enable both the sealing and cutting functions.

11. The medical system of claim 8, further comprising:
a second conductive line disposed adjacent to the second pad and forming a loop substantially around a perimeter of the second pad, wherein the second conductive line is coated with a ferromagnetic coating.

12. A medical method comprising:
operating a multi-functional instrument to perform a heat-generating function, wherein the instrument comprises a shaft, a wrist having movement in two or more directions, and an end effector, the end effector comprising:
a non-bladed first jaw comprising a first pad;
a non-bladed second jaw comprising a second pad; and
at least one conductive line for performing the first heat-generating function disposed adjacent to the first and second pads and forming a loop substantially around a perimeter of the first and second pads;
modifying the instrument to perform a second heat-generating function that is different from the first heat-generating function, wherein the second heat-generating function is performed by the conductive line.

13. The method of claim 12, wherein the first heat-generating function comprises sealing and the second heat-generating function comprises cutting.

14. The medical method of claim 12, wherein the end effector further comprises:
a second conductive line disposed adjacent to the second pad and forming a loop substantially around a perimeter of the second pad, wherein the second conductive line is coated with a ferromagnetic coating.

* * * * *